United States Patent
Schiltz et al.

(10) Patent No.: US 11,919,855 B2
(45) Date of Patent: Mar. 5, 2024

(54) SUBSTITUTED PYRROLIDONES AND PIPERIDONES AS SMALL MOLECULE INHIBITORS OF EZH2 AND EED PROTEIN BINDING

(71) Applicant: Northwestern University, Evanston, IL (US)

(72) Inventors: Gary E. Schiltz, Naperville, IL (US); Jindan Yu, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/733,513

(22) Filed: Apr. 29, 2022

(65) Prior Publication Data

US 2022/0363633 A1    Nov. 17, 2022

Related U.S. Application Data

(60) Provisional application No. 63/201,430, filed on Apr. 29, 2021.

(51) Int. Cl.
  *C07D 207/273* (2006.01)
  *C07D 207/27* (2006.01)

(52) U.S. Cl.
  CPC ....... *C07D 207/273* (2013.01); *C07D 207/27* (2013.01)

(58) Field of Classification Search
  CPC ............ C07D 207/273; C07D 207/27
  See application file for complete search history.

(56) References Cited

U.S. PATENT DOCUMENTS

| | | |
|---|---|---|
| 10,640,502 B2 | 5/2020 | Shilatifard et al. |
| 2016/0002252 A1 | 1/2016 | Schiltz et al. |
| 2016/0052870 A1 | 2/2016 | Schiltz et al. |
| 2016/0214969 A1 | 7/2016 | Siddique et al. |
| 2017/0121326 A1 | 5/2017 | Schiltz et al. |
| 2017/0253581 A1 | 9/2017 | Schiltz et al. |
| 2018/0155295 A1 | 6/2018 | Schiltz et al. |
| 2019/0276458 A1 | 9/2019 | Schiltz et al. |
| 2020/0390894 A1 | 12/2020 | Schiltz et al. |
| 2020/0392116 A1 | 12/2020 | Schiltz et al. |
| 2020/0399241 A1 | 12/2020 | Scheidt et al. |
| 2021/0276960 A1 | 9/2021 | Schiltz et al. |

FOREIGN PATENT DOCUMENTS

| | | | |
|---|---|---|---|
| RU | 2744571 | * | 3/2021 |
| WO | 2019183373 | | 9/2019 |
| WO | 2020092950 | | 5/2020 |
| WO | 2020112846 | | 6/2020 |

OTHER PUBLICATIONS

Kong et al., Astemizole Arrests the Proliferation of Cancer Cells by Disrupting the EZH2-EED Interaction of Polycomb Repressive Complex 2. J. Med Chem. 2014, 57(22), 9512-9521.

* cited by examiner

*Primary Examiner* — Kamal A Saeed
(74) *Attorney, Agent, or Firm* — Quarles & Brady LLP

(57) ABSTRACT

Disclosed are substituted pyrrolidones and piperidones which may be utilized as EZH2 targeting agents. The substituted pyrrolidones and piperidones may include substituted 2-pyrrolidones and 2-piperidones. The disclosed pyrrolidones and piperidones may be used in pharmaceutical compositions and methods for treating cell proliferative disorders such as cancer.

19 Claims, 1 Drawing Sheet

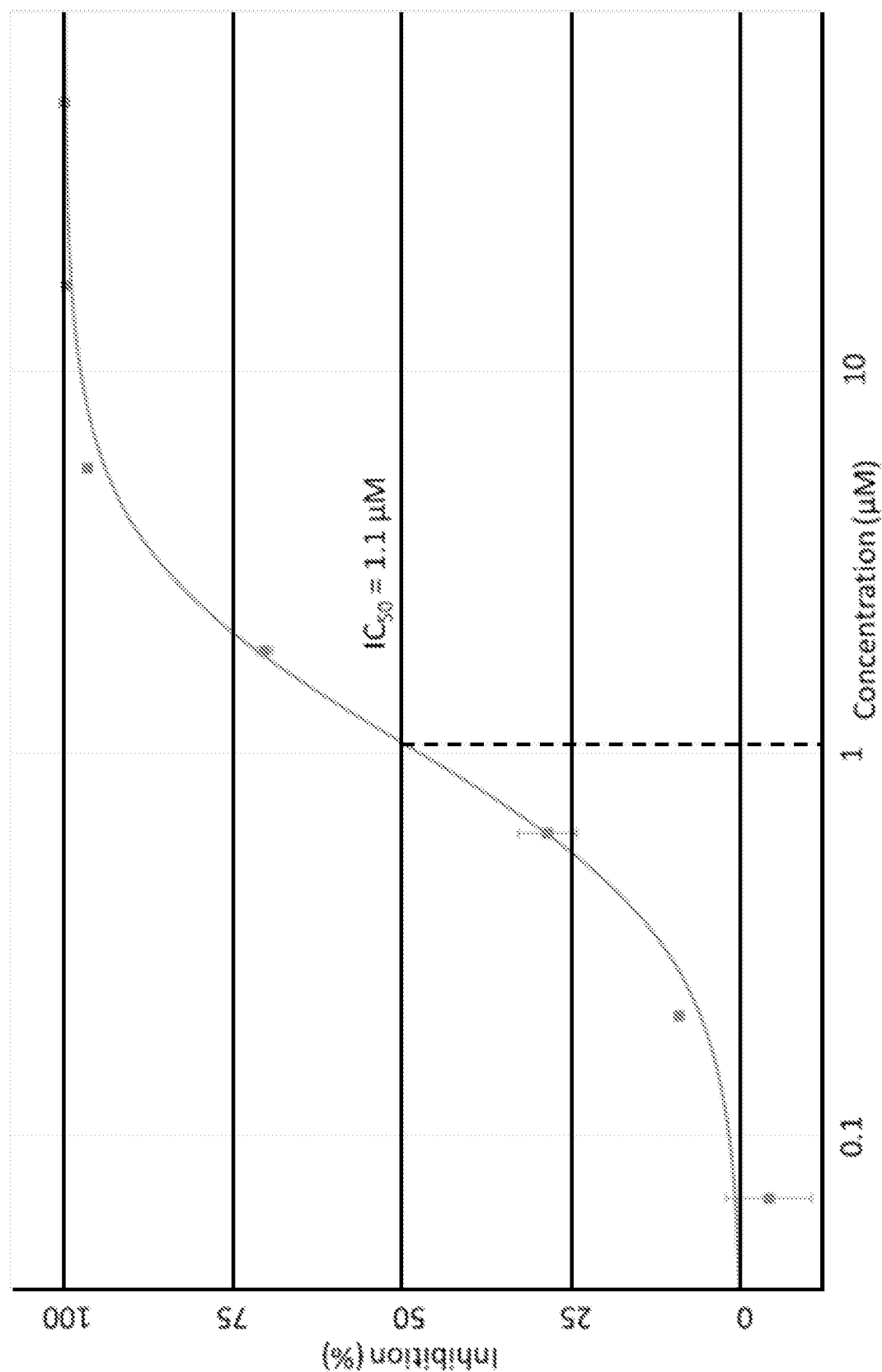

SUBSTITUTED PYRROLIDONES AND PIPERIDONES AS SMALL MOLECULE INHIBITORS OF EZH2 AND EED PROTEIN BINDING

CROSS-REFERENCE TO RELATED APPLICATIONS

The present application claims priority to U.S. Provisional Patent Application No. 63/201,430, filed Apr. 29, 2021, the entire contents of which are hereby incorporated by reference.

STATEMENT REGARDING FEDERALLY SPONSORED RESEARCH

This invention was made with government support under grant number W81XWH-17-1-0405 and W81XWH-17-1-0406 awarded by the U.S. Army Medical Research and Materiel Command. The government has certain rights in the invention.

BACKGROUND OF THE INVENTION

The field of the invention relates to substituted pyrrolidones (5-carbon) and piperidones (6-carbon) as small molecule inhibitors of enhancer of zeste homolog 2 (EZH2) and embryonic ectoderm development (EED) protein binding. In particular, the field of the invention relates to substituted 2-pyrrolidones and 2-piperidones as EZH2 and EED protein binding agents for the treatment of cell proliferation diseases and disorders such as cancer.

The protein EZH2 is an essential component of the PRC2 complex. This protein is a methyltransferase enzyme that produces H3K27me3. Aberrant EZH2 leads to tumor growth and is a well-validated target in a variety of cancers. In addition to its enzymatic function, EZH2 is also able to increase tumor cell proliferation in a non-enzymatic manner. Because of this, enzyme inhibitors may not fully abolish all of its oncogenic functions. For EZH2 to be catalytically active, it must be part of a functional and intact PRC2 complex. The PRC2 complex also provides stability to EZH2 and reduces its turnover in the cell. Disruption of the PRC2 complex or preventing its formation is expected to block the ability of EZH2 to catalyze methyltransferase activity as well as lead to increased EZH2 protein degradation. Because of this, the present invention develops and provides a series of small molecules that bind to EZH2 and block its ability to bind EED. This inhibition is expected to prevent formation and retention of a PRC2 complex, and thereby lead to inhibition of EZH2 activity and its accelerated degradation.

EZH2 is a very well validated cancer target. Previously, Kong et al. have demonstrated that astemizole arrests the proliferation of cancer cells by disrupting the EZH2-EED interaction of polycomb repressive complex 2 (J. Med. Chem. 2014, 57(22), 9512-9521.). Existing EZH2 inhibitors require very high doses to sufficiently inhibit enzyme activity. Substituted pyrrolidones and piperidones of the present invention inhibit EZH2-EED interaction, which is expected to prevent PRC2 complex formation. This leads to inhibition of EZH2 and degradation of EZH2, which will abolish all functions (both catalytic and non-catalytic) of EZH2. These characteristics suggest substituted pyrrolidones and piperidones of the present invention will have far superior efficacy than existing EZH2 drugs such as tazemostat.

Substituted pyrrolidones and piperidones of the present invention will provide superior efficacy by blocking both catalytic and non-catalytic EZH2 functions. Substituted pyrrolidones and piperidones of the present invention may possess improved safety profiles by being selective for the EZH2-EED interaction, instead of other EZH2 catalytic inhibitors which may act against other methyltransferases and give off-target effects.

BRIEF SUMMARY OF THE INVENTION

Disclosed are substituted pyrrolidones and piperidones which may be utilized as EZH2 targeting agents. The substituted pyrrolidones and piperidones may include substituted 2-pyrrolidones and 2-piperidones. The disclosed pyrrolidones and piperidones may be used in pharmaceutical compositions and methods for treating cell proliferative disorders such as cancer.

The disclosed substituted heterocycles may include substituted pyrrolidones and piperidones having a formula I:

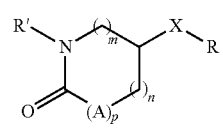

wherein
m is 0-2, n is 0-1, and p is 0-1, with the proviso that (m+n+p) is 2 or 3;
A is —C(R$^1$)(R$^2$)—;
X is selected from —N(R$^3$)—C(O)—, —N(R$^3$)—CH$_2$—, —CH$_2$—N(R$^3$)—C(O)—, —N(R$^3$)—C(O)—CH$_2$—, —N(R$^3$)—, —N(R$^3$)—S(O)(O)—, and —C(O)—N(R$^3$)—;
R$^1$, R$^2$, and R$^3$ are independently selected from hydrogen and alkyl (e.g., methyl);
R and R' are independently selected from hydrogen, alkyl (e.g., methyl or t-butyl), hydroxyalkyl, cycloalkyl (e.g., cyclohexyl), heterocycloalkyl (e.g., piperidinyl), alkyl(heterocycloalkyl), aryl (e.g., phenyl or naphthyl), heteroaryl (e.g., pyridinyl, pyrimidinyl, quinolinyl, isoquinolinyl, indanyl, indenyl, indolyl, benzofuranyl, furazanyl, thiazolyl, benzimidazolyl, indazolyl, and quinazolinyl), alkyl(aryl) (e.g., benzyl), and alkyl(heteroaryl), and R and R' optionally are substituted at one or more positions with a substituent selected from alkyl (e.g., methyl), alkoxy (e.g., methoxy), halogen (e.g., fluoro, chloro, bromo), haloalkyl (e.g., trifluoromethyl), amino, cyano, nitro, aryl, hydroxyl, carboxyl, carboxy(alkyl) ester, acyl (e.g., acetyl), and oxo.

The disclosed compounds may exhibit one or more biological activities. The disclosed compounds may inhibit binding of the EZH2 protein in the PRC2 complex. The disclosed compounds may inhibit the growth of cells that express EZH2 protein (preferably by at a concentration of less than about 100 µM, 50 µM, 10 µM, 1 µM, 0.1 µM, 0.05 µM, 0.01 µM, 0.005 µM, 0.001 µM, or less). The disclosed compounds may not inhibit the growth of cells that do not express EZH2 protein (preferably at a concentration of greater than about 0.001 µM, 0.005 µM, 0.01 µM, 0.5 µM, 0.1 µM, 1.0 µM, 10 µM, and 100 µM or higher).

In some embodiments, the disclosed compounds inhibit binding of EZH2 protein in the PRC2 complex. For example, the disclosed compounds may inhibit binding of EZH2 to EED. In some embodiments, the disclosed compounds inhibit binding of EZH2 protein in the PRC2 complex but do not inhibit the enzymatic activity of EZH2.

Also disclosed are pharmaceutical compositions comprising the disclosed compounds and a suitable pharmaceutical carrier, excipient, or diluent. The disclosed pharmaceutical compositions may comprise an effective amount of the compound for inhibiting the growth of cancer cells when administered to a subject in need thereof.

Also disclosed are methods for treating cell proliferation diseases and disorders such as cancer. The methods may include administering the disclosed compounds or pharmaceutical compositions comprising the disclosed compounds to a subject in need thereof, for example, to a subject having cancer. The disclosed compounds or pharmaceutical compositions comprising the disclosed compounds may be administered with additional therapeutic agents, optionally in combination, in order to treat cell proliferative diseases and disorders. Cell proliferative diseases and disorders treated by the disclosed methods may include, but are not limited to, cancers selected from the group consisting of lymphoma, bladder cancer, multiple myeloma, leukemia, non-small cell lung cancer, colon cancer, cancer of the central nervous system (e.g., glioblastoma), melanoma, pancreatic cancer, ovarian cancer, renal cancer, prostate cancer, and breast cancer.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 1 shows an exemplary concentration-response curve for NUCC-0226245.

DETAILED DESCRIPTION OF THE INVENTION

The present invention is described herein using several definitions, as set forth below and throughout the application.

Unless otherwise specified or indicated by context, the terms "a", "an", and "the" mean "one or more." For example, "a compound" and "a substituent" should be interpreted to mean "one or more compounds" and "one or more substituents," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment.

A "subject in need of treatment" may include a subject having a disease, disorder, or condition that is responsive to therapy with a substituted pyrrolidone or piperidone such as the presently disclosed substituted pyrrolidones and piperidones. For example, a "subject in need of treatment" may include a subject having a cell proliferative disease, disorder, or condition such as cancer (e.g., cancers such as lymphoma, bladder cancer, multiple myeloma, leukemia, non-small cell lung cancer, colon cancer, cancer of the central nervous system, melanoma, ovarian cancer, renal cancer, prostate cancer, and breast cancer). A "subject in need of treatment" may include a subject having a cell proliferative disease, disorder, or condition such as cancer that is associated with EZH2 activity and/or that may be treated by administering an effective amount of an agent that modulates EZH2 activity. A "subject in need of treatment" may include a subject having a cell proliferative disease, disorder, or condition such as cancer that is associated with EZH2 activity and/or that may be treated by administering an effective amount of an agent that modulates EZH2 stability and/or half-life.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "modulate" means decreasing or inhibiting activity and/or increasing or augmenting activity. For example, modulating EZH2 activity may mean increasing or augmenting EZH2 activity and/or decreasing or inhibiting EZH2 activity. The compounds disclosed herein may be administered to modulate EZH2 activity.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched $C_1$-C6 alkyl group). Exemplary alkylene groups include, but are not limited to —$CH_2$—, —$CH_2CH_2$—, —$CH_2CH_2CH_2$—, —$CH(CH_3)CH_2$—, —$CH_2CH(CH_3)CH_2$—, —$CH(CH_2CH_3)CH_2$—, and the like.

The term "haloalkyl" refers to an alkyl group that is substituted with at least one halogen. For example, —CH$_2$F, —CHF2, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3-to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Substituted Pyrrolidones and Piperidones and Uses Thereof for Inhibiting the Biological Activity of EZH2

Disclosed herein are substituted pyrrolidones and piperidones. The disclosed heterocycles have been shown to inhibit the biological activity of EZH2. The disclosed substituted heterocycles may include substituted pyrrolidones and substituted piperidones.

In some embodiments, the disclosed substituted heterocycles may include substituted pyrrolidones or piperidones having a formula I:

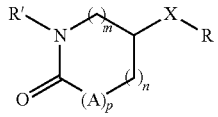

wherein m is 0-2, n is 0-1, and p is 0-1, with the proviso that (m+n+p) is 2 or 3;

A is —C(R$^1$)(R$^2$)—;

X is selected from —N(R$^3$)—C(O)—, —N(R$^3$)—CH$_2$—, —CH$_2$—N(R$^3$)—C(O)—, —N(R$^3$)—C(O)—CH$_2$—, —N(R$^3$)—, —N(R$^3$)—S(O)(O)—, and —C(O)-N(R$^3$)—;

R$^1$, R$^2$, and R$^3$ are independently selected from hydrogen and alkyl (e.g., methyl);

R and R' are independently selected from hydrogen, alkyl (e.g., methyl or t-butyl), hydroxyalkyl, cycloalkyl (e.g., cyclohexyl), heterocycloalkyl (e.g., piperidinyl), alkyl(heterocycloalkyl), aryl (e.g., phenyl or naphthyl), heteroaryl (e.g., pyridinyl, pyrimidinyl, quinolinyl, isoquinolinyl, indanyl, indenyl, indolyl, benzofuranyl, furazanyl, thiazolyl, benzimidazolyl, indazolyl, and quinazolinyl), alkyl(aryl) (e.g., benzyl), and alkyl(heteroaryl), and R and R' optionally are substituted at one or more positions with a substituent selected from alkyl (e.g., methyl), alkoxy (e.g., methoxy), halogen (e.g., fluoro, chloro, bromo), haloalkyl (e.g., trifluoromethyl), amino, cyano, nitro, aryl, hydroxyl, carboxyl, carboxy(alkyl) ester, acyl (e.g., acetyl), and oxo.

In some embodiments of these disclosed substituted pyrrolidones and piperidones, m=1, n=0, p=1, A is —C(R$^1$)(R$^2$)—, X is —CH$_2$—N(R$^3$)—C(O)—, R is aryl (e.g., phenyl or naphthyl), and R' is alkyl(aryl) (e.g., benzyl). In some embodiments of the disclosed compounds, R$^1$, R$^2$, and R$^3$ are hydrogen, R is phenyl, and R' is benzyl. In some embodiments of the disclosed compounds, R is substituted with at least one hydroxyl and at least one haloalkyl, and R' is substituted with at least one haloalkyl. In some embodiments of the disclosed compounds, R is substituted with one hydroxyl and one trifluoromethyl, and R' is substituted with one trifluoromethyl.

In some embodiments of these disclosed substituted pyrrolidones and piperidones, m=1, n=0, p=1, A is —C(R$^1$)(R$^2$)—, X is —N(R$^3$)—C(O)—, R is aryl (e.g., phenyl or naphthyl), and R' is alkyl(aryl) (e.g., benzyl). In some embodiments of the disclosed compounds, R$^1$ and R$^2$ are alkyl or hydrogen, R$^3$ is hydrogen, R is phenyl, and R' is benzyl. In some embodiments of the disclosed compounds, R$^1$ and R$^2$ are methyl. In some embodiments of the disclosed compounds, R is substituted with at least one haloalkyl and at least one hydroxyl, and R' is substituted with at least one haloalkyl. In some embodiments of the disclosed compounds, R is substituted with one hydroxyl and one trifluoromethyl, and R' is substituted with one trifluoromethyl.

In some embodiments of these disclosed substituted pyrrolidones and piperidones, m=2, n=0, p=0, X is —N(R$^3$)—C(O)—, R is aryl (e.g., phenyl or naphthyl), and R' is alkyl(aryl) (e.g., benzyl). In some embodiments of the disclosed compounds, R$^3$ is hydrogen, R is phenyl, and R' is benzyl. In some embodiments of the disclosed compounds, R is substituted with at least one haloalkyl and at least one hydroxyl, and R' is substituted with at least one haloalkyl. In some embodiments of the disclosed compounds, R is substituted with one hydroxyl and one trifluoromethyl, and R' is substituted with one trifluoromethyl.

The formulae of the compounds disclosed herein should be interpreted as encompassing all possible stereoisomers, enantiomers, or epimers of the compounds unless the formulae indicate a specific stereoisomer, enantiomer, or epimer. The formulae of the compounds disclosed herein should be interpreted as encompassing salts, esters, amides, or solvates thereof of the compounds.

Use of the Disclosed Compounds for Inhibiting EZH2 Activity

The disclosed compounds may exhibit one or more biological activities. The disclosed compounds may inhibit binding of EZH2 to EED protein. In some embodiments, the disclosed compounds inhibit binding of EZH2 to EED protein by at least 50%, 60%, 70%, 80%, 90%, 95%, 96%, 97%, 98%, or 99% at a concentration of less than about 100 μM, 50 μM, 10 μM, 1 μM, 0.1 μM, 0.05 μM, 0.01 μM, 0.005 μM, 0.001 μM, or less. The disclosed compounds may inhibit the growth of cells that express EZH2 (preferably by at least 50%, 60%, 70%, 80%, 90%, 95%, 96%, 97%, 98%, or 99% at a concentration of less than about 100 μM, 50 μM, 10 μM, 1 μM, 0.1 μM, 0.05 μM, 0.01 μM, 0.005 μM, 0.001 μM, or less). The disclosed compounds may not inhibit the growth of cells that do not express EZH2 (preferably by not more than 50%, 40%, 30%, 20%, 10%, 5%, 4%, 3%, 2% or less at a concentration of greater than about 0.001 μM, 0.005 μM, 0.01 μM, 0.5 μM, 0.1 μM, 1.0 μM, 10 μM, and 100 μM or higher). Concentration ranges also are contemplated herein, for example, a concentration range bounded by end-point concentrations selected from 0.001 μM, 0.005 μM, 0.01 μM, 0.5 μM, 0.1 μM, 1.0 μM, 10 μM, and 100 μM.

The disclosed compounds may be effective in inhibiting cell proliferation of cancer cells, including cancer cells that express EZH2 and whose proliferation is inhibiting by inhibiting the biological activity of EZH2. The disclosed compounds may be effective in inhibiting cell proliferation of one or more types of cancer cells including: lymphoma cells, such as; bladder cancer cells, such as; multiple myeloma cells, such as MM.1S cells; leukemia cells, such as CCRF-CEM, HL-60(TB), MOLT-4, RPMI-8226 and SR; non-small lung cancer cells, such as A549/ATCC, EKVX, HOP-62, HOP-92, NCI-H226, NCI-H23, NCI-H322M, NCI-H460 and NCI-H522; colon cancer cells, such as COLO 205, HCC-2998, HCT-116, HCT-15, HT29, KM12 and SW-620; CNS: SF-268, SF-295, SF-539, SNB-19, SNB-75 and U251; melanoma cancer cells, such as LOX IMVI, MALME-3M, M14, MDA-MB-435, SK-MEL-2, SK-MEL-28, SK-MEL-5, UACC-257 and UACC-62; ovarian cancer cells, such as IGR-OV1, OVCAR-3, OVCAR-4, OVCAR-5, OVCAR-8, NCI/ADR-RES and SK-OV-3; renal cancer cells, such as 786-0, A498, ACHN, CAKI-1, RXF 393, SN12C, TK-10 and UO-31; prostate cancer cells, such as DU-145 and PC-3; and breast cancer cells, such as MCF7, MDA-MB-231/ATCC, MDA-MB-468, HS 578T, BT-549 and T-47D.

Cell proliferation and inhibition thereof by the presently disclosed compounds may be assessed by cell viability methods disclosed in the art including colorimetric assays that utilize dyes such as MTT, XTT, and MTS to assess cell viability. Preferably, the disclosed compounds have an $IC_{50}$ of less than about 10 µM, 5 µM, 1 µM, 0.5 µM, 0.01 µM, 0.005 µM, 0.001 µM or lower in the selected assay.

The disclosed compounds may be formulated as anti-cancer therapeutics, including hematologic malignancies, breast, lung, pancreas and prostate malignancies. The disclosed compounds also may be formulated as anti-inflammation therapeutics.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µM).

The disclosed compounds and pharmaceutical compositions comprising the disclosed compounds may be administered in methods of treating a subject in need thereof. For example, in the methods of treatment a subject in need thereof may include a subject having a cell proliferative disease, disorder, or condition such as cancer (e.g., cancers such as lymphoma, bladder cancer, multiple myeloma, leukemia, non-small cell lung cancer, colon cancer, cancer of the central nervous system, melanoma, ovarian cancer, renal cancer, prostate cancer, and breast cancer).

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds for achieving therapy in the disclosed methods of treatment may include dose levels falling within ranges having as end-points any of these disclosed dose levels (e.g., 500-2000 ng/kg body weight of the subject).

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and crosslinked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules. In some embodiments, the compounds are formulated as a composition for administration orally (e.g., in a solvent such as 5% DMSO in oil such as vegetable oil).

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Combination Therapies and Pharmaceutical Compositions

The disclosed compounds or pharmaceutical compositions comprising the disclosed compounds may be administered in methods of treatment. For example, the disclosed compounds or pharmaceutical compositions comprising the disclosed compounds may be administered in methods of treating cell proliferative diseases and disorders. Cell proliferative diseases and disorders treated by the disclosed methods may include, but are not limited to, cancers selected from the group consisting of multiple lymphoma, bladder cancer, myeloma, leukemia, non-small cell lung cancer, colon cancer, cancer of the central nervous system, melanoma, ovarian cancer, renal cancer, prostate cancer, and breast cancer.

Optionally, the disclosed compounds or pharmaceutical compositions comprising the disclosed compounds may be administered with additional therapeutic agents, optionally in combination, in order to treat cell proliferative diseases and disorders. In some embodiments of the disclosed methods, one or more additional therapeutic agents are administered with the disclosed compounds or with pharmaceutical compositions comprising the disclosed compounds, where the additional therapeutic agent is administered prior to, concurrently with, or after administering the disclosed compounds or the pharmaceutical compositions comprising the disclosed compounds. In some embodiments, the disclosed pharmaceutical composition are formulated to comprise the disclosed compounds and further to comprise one or more additional therapeutic agents, for example, one or more additional therapeutic agents for treating cell proliferative diseases and disorders.

Illustrative Embodiments

Embodiment 1. A compound having a formula I:

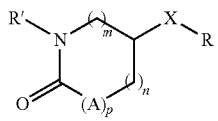

wherein
m is 0-2, n is 0-1, and p is 0-1, with the proviso that (m+n+p) is 2 or 3;
A is —C($R^1$)($R^2$)—;
X is selected from —N($R^3$)—C(O)—, —N($R^3$)—$CH_2$—, —$CH_2$—N($R^3$)—C(O)—, —N($R^3$)—C(O)—$CH_2$—, —N($R^3$)—, —N($R^3$)—S(O)(O)—, and —C(O)—N($R^3$)—;
$R^1$, $R^2$, and $R^3$ are independently selected from hydrogen and alkyl (e.g., methyl); and R and R' are independently selected from hydrogen, alkyl, hydroxyalkyl, cycloalkyl, heterocycloalkyl, alkyl(heterocycloalkyl), aryl, heteroaryl, alkyl(aryl), and alkyl(heteroaryl), and R and R' optionally are substituted at one or more positions with a substituent selected from alkyl, alkoxy, halogen, haloalkyl, amino, cyano, nitro, aryl, hydroxyl, carboxyl, carboxy(alkyl) ester, acyl, and oxo.

Embodiment 2. The compound of embodiment 1, wherein m=1, n=0, p=1, A is —C($R^1$)($R^2$)—, X is —$CH_2$—N($R^3$)—C(O)—, R is aryl, and R' is alkyl(aryl).

Embodiment 3. The compound of embodiment 1 or 2, wherein $R^1$, $R^2$, and $R^3$ are hydrogen, R is phenyl, and R' is benzyl.

Embodiment 4. The compound of any of the foregoing embodiments, wherein R is substituted with at least one hydroxyl and at least one haloalkyl, and R' is substituted with at least one haloalkyl.

Embodiment 5. The compound of any of the foregoing embodiments, wherein R is substituted with one hydroxyl and one trifluoromethyl, and R' is substituted with one trifluoromethyl.

Embodiment 6. The compound of any of the foregoing embodiments, wherein m=1, n=0, p=1, A is —C($R^1$)($R^2$)—, X is —N($R^3$)—C(O)—, R is aryl, R' is alkyl(aryl).

Embodiment 7. The compound of any of the foregoing embodiments, wherein $R^1$ and $R^2$ are alkyl or hydrogen, $R^3$ is hydrogen, R is phenyl, and R' is benzyl.

Embodiment 8. The compound of any of the foregoing embodiments, wherein $R^1$ and $R^2$ are methyl.

Embodiment 9. The compound of any of the foregoing embodiments, wherein R is substituted with at least one haloalkyl and at least one hydroxyl, and R' is substituted with at least one haloalkyl.

Embodiment 10. The compound of any of the foregoing embodiments, wherein R is substituted with one hydroxyl and one trifluoromethyl, and R' is substituted with one trifluoromethyl.

Embodiment 11. The compound of any of the foregoing embodiments, wherein m=2, n=0, p=0, X is —N($R^3$)—C(O)—, R is aryl, and R' is alkyl(aryl).

Embodiment 12. The compound of any of the foregoing embodiments, wherein $R^3$ is hydrogen, R is phenyl, and R' is benzyl.

Embodiment 13. The compound of any of the foregoing embodiments, wherein R is substituted with at least one haloalkyl and at least one hydroxyl, and R' is substituted with at least one haloalkyl.

Embodiment 14. The compound of any of the foregoing embodiments, wherein R is substituted with one hydroxyl and one trifluoromethyl, and R' is substituted with one trifluoromethyl.

Embodiment 15. A compound having a formula as presented in this application.

Embodiment 16. A compound having a formula selected from:

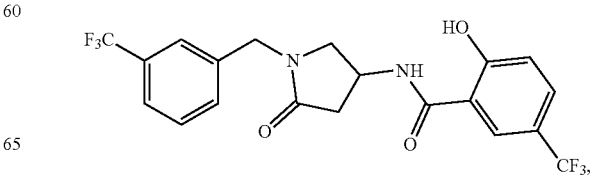

15

-continued

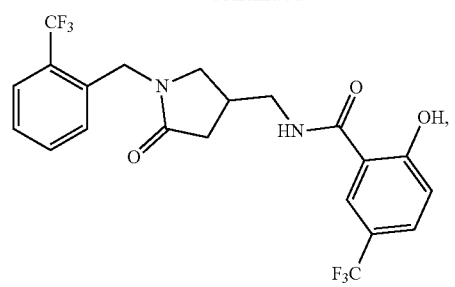

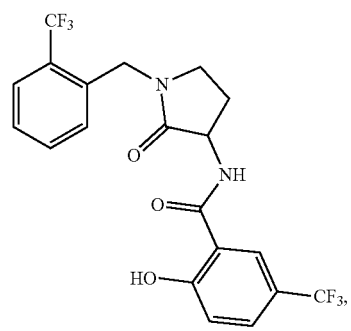

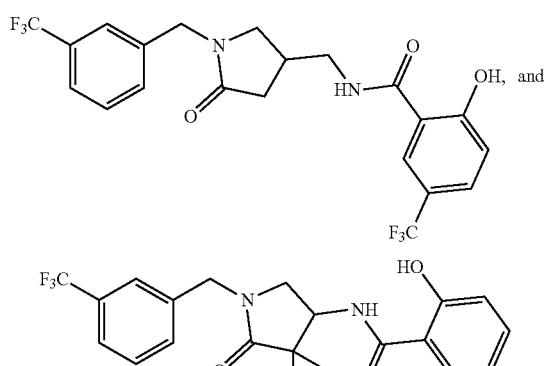

Embodiment 17. A pharmaceutical composition comprising a compound of any of the foregoing embodiments and a suitable pharmaceutical carrier, excipient, or diluent.

Embodiment 18. A method of treating cancer in a subject in need thereof, the method comprising administering the composition of embodiment 17 to the subject.

Embodiment 19. The method of embodiment 18, wherein the cancer is associated with binding of enhancer of zeste homolog 2 (EZH2) and embryonic ectoderm development (EED) protein, and the compound inhibits binding of EZH2 and EED but does not inhibit enzymatic activity of EZH2.

Embodiment 20. The method of embodiment 19, wherein the cancer is selected from lymphoma, bladder cancer, multiple myeloma, leukemia, non-small cell lung cancer, colon cancer, cancer of the central nervous system, melanoma, ovarian cancer, renal cancer, prostate cancer, and breast cancer.

EXAMPLES

The following Examples are illustrative and are not intended to limit the scope of the claimed subject matter.

16

Example 1

Preparation of Exemplary Substituted Pyrrolidones and Piperidones

Table 1 shows representative substituted pyrrolidones and piperidones. Exemplary methods for preparing the substituted pyrrolidones and piperidones are shown below.

Generic Scheme for the Synthesis of Substituted Pyrrolidones

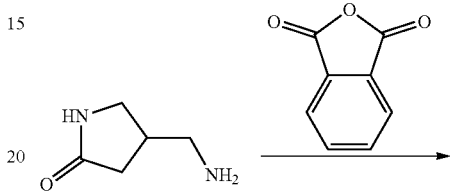

1

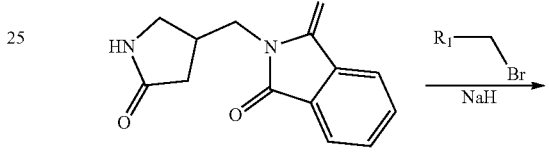

2

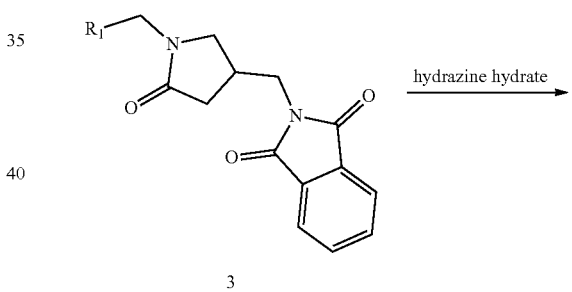

3

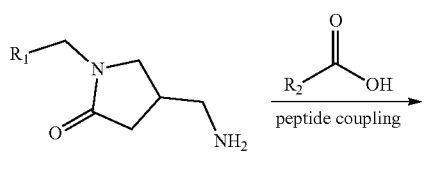

4

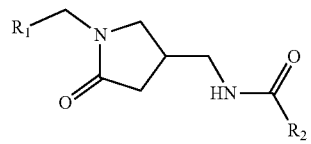

5

Synthesis of Substituted Pyrrolidones and Piperidones

Analog compounds were synthesized according to the generic scheme above. Procedures for NUCC-0202749 and NUCC-0226244 are described here in detail.

Synthesis of NUCC-0202749

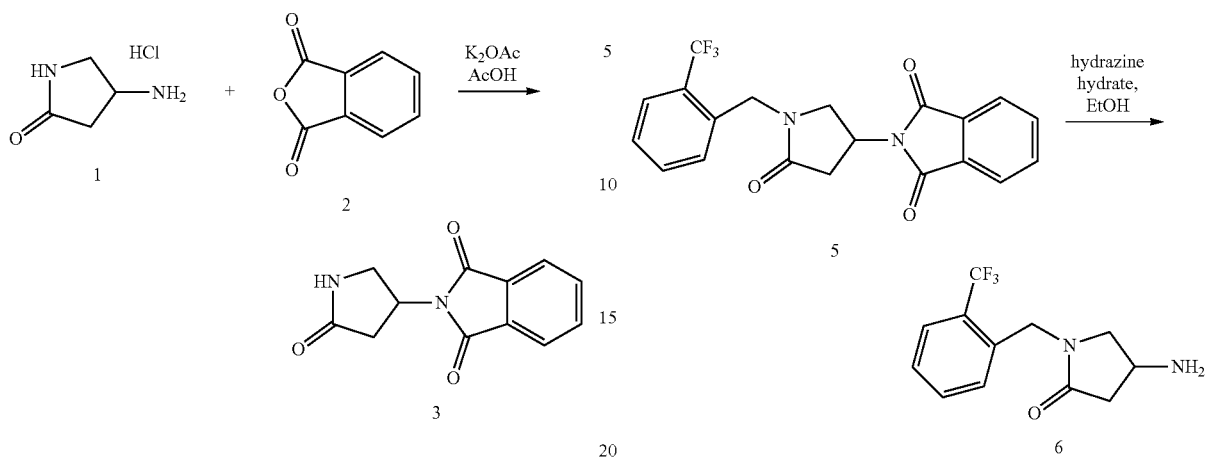

Synthesis of 2-(5-oxopyrrolidin-3-yl)isoindoline-1,3-dione (3). To a solution containing 4-aminopyrrolidin-2-one hydrochloride (102.4 mg, 1 Eq, 749.4 μmol) and isobenzofuran-1,3-dione (111.0 mg, 1 Eq, 749.4 μmol) in AcOH (3 mL) was added potassium acetate (183.9 mg, 2.5 Eq, 1.873 mmol). The solution was refluxed and reaction completed after 1 h. The solution was cooled to rt, concentrated in vacuo, and used as-is.

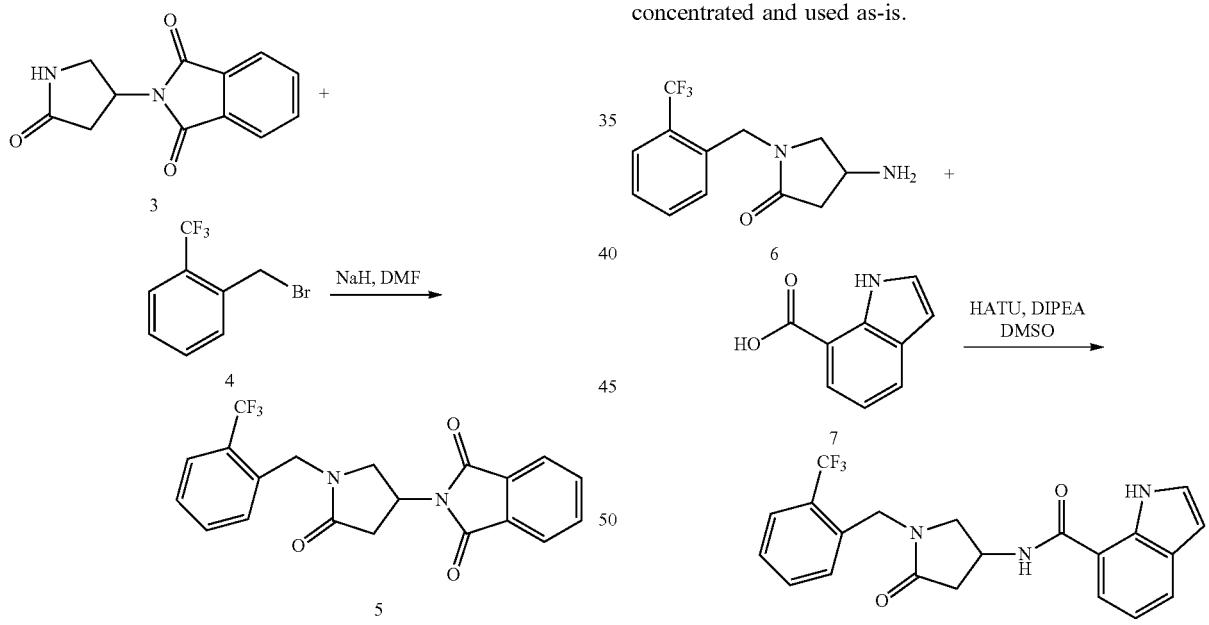

Synthesis of 2-(5-oxo-1-(2-(trifluoromethyl)benzyl)pyrrolidin-3-yl)isoindoline-1,3-dione (5). A solution containing 2-(5-oxopyrrolidin-3-yl)isoindoline-1,3-dione (1.012 g, 4.41 mmol) in DMF (5 mL) was cooled to 0° C. before the addition of NaH (60% in mineral oil, 0.26 g, 1.5 Eq, 6.61 mmol). After 10 min, 1-(bromomethyl)-2-(trifluoromethyl)benzene (1.58 g, 1.5 Eq, 6.61 mmol) was added and the reaction was stirred at rt. Upon completion, the reaction was quenched with saturated ammonium chloride and crude product extracted with 5% DCM/MeOH. The organic layer was dried over anhydrous sodium sulfate and concentrated. The crude product was dry loaded onto Biotage KP-Sil 50 g column and eluted with 0-5% MeOH/DCM over 20 CV to afford the title compound (1.0 g, 58%).

Synthesis of 4-amino-1-(2-(trifluoromethyl)benzyl)pyrrolidin-2-one (6). A solution containing 2-(5-oxo-1-(2-(trifluoromethyl)benzyl)pyrrolidin-3-yl)isoindoline-1,3-dione (246 mg, 633 μmol) in EtOH (1.1 mL) was heated to 80° C. before the addition of hydrazine hydrate (205 μL, 4.0 Eq, 2.53 mmol). The reaction was refluxed for 1 h and monitored by LC-MS. Upon completion, the reaction was allowed to cool to rt, filtered and washed with DCM. The filtrate was concentrated and used as-is.

Synthesis of N-(5-oxo-1-(2-(trifluoromethyl)benzyl)pyrrolidin-3-yl)-1H-indole-7-carboxamide (8, NUCC-0202749). A solution containing 1H-indole-7-carboxylic acid (11.0 mg, 1 Eq, 68.3 μmol), HATU (26.0 mg, 68.3 1.000 molar, 1 Eq, 68.3 μmol), and DIPEA (26.5 mg, 36 μL, 3.0 Eq, 205 μmol) in 100 μL DMSO was stirred for 5 min before addition of 4-amino-1-(2-(trifluoromethyl)benzyl)pyrrolidin-2-one (35.3 mg, 137 1.000 molar, 2.0 Eq, 137 μmol) in DMSO. The reaction was monitored by LCMS. Upon completion, the reaction was diluted with acetonitrile and purified by prep-HPLC using 10-90% ACN with 0.1% formic acid to afford the title compound (12.3 mg, 45%).

¹H-NMR (500 MHz, Chloroform-d) δ 10.19 (s, 1H), 7.79 (d, J=7.8 Hz, 1H), 7.61 (d, J=7.8 Hz, 1H), 7.47-7.39 (m, 3H), 7.32 (td, J=7.2, 6.5, 2.2 Hz, 1H), 7.28 (t, J=2.8 Hz, 1H), 7.07 (t, J=7.7 Hz, 2H), 6.54 (t, J=2.7 Hz, 1H), 4.77 (tq, J=9.7, 6.4, 4.9 Hz, 1H), 4.70 (d, J=2.6 Hz, 2H), 3.71 (dd, J=10.8, 6.5 Hz, 1H), 3.28 (dd, J=10.7, 3.2 Hz, 1H), 2.96 (dd, J=17.3, 8.2 Hz, 1H), 2.58 (dd, J=17.4, 3.9 Hz, 1H).

Synthesis of NUCC-0226244

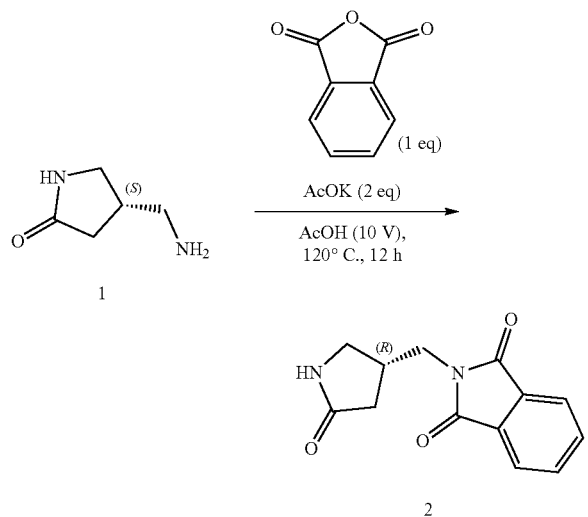

To a solution of Compound 1 (900 mg, 5.98 mmol, 1 eq, HCl salt) and isobenzofuran-1,3-dione (885.11 mg, 5.98 mmol, 1 eq) in AcOH (9 mL) was added AcOK (1.17 g, 11.95 mmol, 2 eq), the reaction was stirred at 120° C. for 12 hrs. LCMS showed all the starting material was consumed and a new peak with desired product MS was detected. The reaction mixture was concentrated under reduced pressure to give a residue, which was purified by chromatography on silica gel (eluted with dichloromethane/methanol=50/1 to 10/1) to give Compound 2 (900 mg, yield 59.81%) as a white solid.

¹H NMR (400 MHz, CHLOROFORM-d) δ 2.21 (dd, J=17.01, 7.00 Hz, 1H), 2.47 (dd, J=17.07, 8.82 Hz, 1H), 2.97 (dt, J=14.54, 7.30 Hz, 1H), 3.25 (dd, J=9.88, 5.88 Hz, 1H), 3.49 (dd, J=9.69, 8.07 Hz, 1H), 3.79 (dd, J=7.19, 3.56 Hz, 2H), 6.34 (br s, 1H), 7.69-7.80 (m, 2H), 7.82-7.90 (m, 2H)

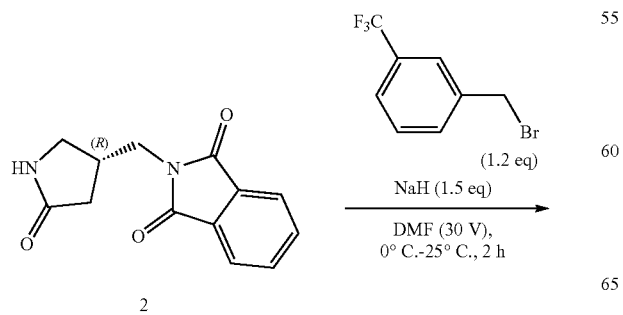

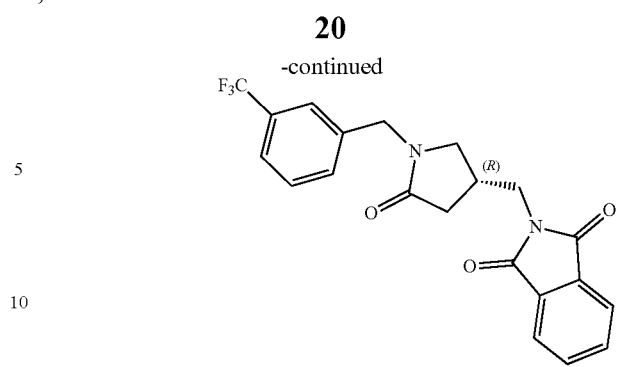

To a solution of Compound 2 (900 mg, 3.68 mmol, 1 eq) in DMF (27 mL) was added NaH (221.07 mg, 5.53 mmol, 60% purity, 1.5 eq) at 0° C., the mixture was stirred at 0° C. for 30 mins, then 1-(bromomethyl)-3-(trifluoromethyl)benzene (1.06 g, 4.42 mmol, 673.22 uL, 1.2 eq) was added at 0° C., the reaction was stirred at 20° C. for 2 hrs. LCMS showed about 28% of the starting material was remaining and a new peak (40%) desired product was detected. The reaction mixture was quenched with saturated solution of ammonium chloride (30 mL). The organic phase was separated and the aqueous layer was extracted with ethyl acetate (3×15 mL). The combined organic layers were dried over sodium sulfate, filtered and concentrated under reduced pressure to give a residue, which was purified by chromatography on silica gel (eluted with petroleum ether/tetrahydrofuran=50/1 to 1/1) to give Compound 3 (450 mg, yield 28.83%) as a colorless oil.

¹H NMR (400 MHz, CHLOROFORM-d) δ 2.35 (dd, J=17.00, 6.84 Hz, 1H), 2.59-2.69 (m, 1H), 2.85 (dquin, J=14.71, 7.30 Hz, 1H), 3.15 (dd, J=9.91, 5.77 Hz, 1H), 3.34 (dd, J=9.85, 7.97 Hz, 1H), 3.75 (d, J=7.15 Hz, 2H), 4.33 (d, J=14.93 Hz, 1H), 4.68 (d, J=14.93 Hz, 1H), 7.42-7.50 (m, 3H), 7.55 (br d, J=6.90 Hz, 1H), 7.72-7.78 (m, 2H), 7.83-7.87 (m, 2H)

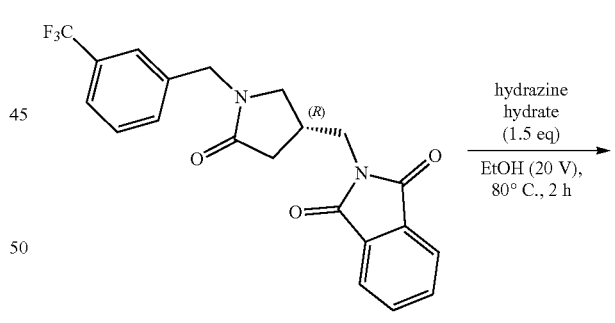

To a solution of Compound 3 (450 mg, 1.12 mmol, 1 eq) in EtOH (9 mL) was added NH2NH2.H2O (83.98 mg, 1.68 mmol, 81.53 uL, 1.5 eq), the mixture was stirred at 80° C. for 2 hrs. LCMS showed all the starting material was consumed and a new peak with desired product MS was detected. The reaction mixture was filtered and the filtrate was concentrated under reduced pressure to give Compound 4 (200 mg, yield 62.4%) as a colorless oil, which was used to the next step directly without further purification.

¹H NMR (400 MHz, CHLOROFORM-d) δ 2.23 (dd, J=16.88, 6.46 Hz, 1H), 2.34-2.46 (m, 1H), 2.58-2.73 (m, 2H), 2.75-2.83 (m, 1H), 3.04 (dd, J=9.79, 5.52 Hz, 1H), 3.40 (dd, J=9.72, 8.09 Hz, 1H), 4.51 (s, 2H), 7.42-7.50 (m, 3H), 7.56 (br d, J=7.03 Hz, 1H)

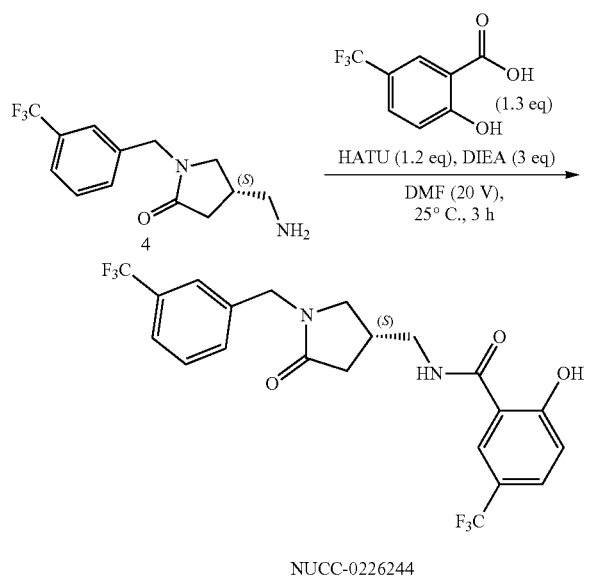

NUCC-0226244

To a solution of 2-hydroxy-5-(trifluoromethyl)benzoic acid (196.83 mg, 954.95 umol, 1.3 eq) and DIEA (284.82 mg, 2.20 mmol, 383.85 uL, 3 eq) in DMF (4 mL) was added HATU (335.17 mg, 881.49 umol, 1.2 eq) in portions at 0° C., the mixture was stirred at 20° C. for 1 hour. Then Compound 4 (200 mg, 734.58 umol, 1 eq) was added, the reaction mixture was stirred at 20° C. for 2 hrs. HPLC showed all the starting material was consumed and about 45% of desired product was detected. The mixture was purified by Prep-HPLC (column: Phenomenex Luna 80*30 mm*3 um; mobile phase: [water (TFA)-ACN]; B %: 40%-70%, 8 mins) to give NUCC-0226244 (78.1 mg, yield 18.51%) as a white solid.

¹H NMR (400 MHz, CHLOROFORM-d) δ 2.43 (br dd, J=16.82, 4.57 Hz, 1H), 2.67-2.87 (m, 2H), 3.15 (dd, J=10.19, 4.19 Hz, 1H), 3.37-3.54 (m, 2H), 3.60 (dt, J=13.38, 6.44 Hz, 1H), 4.44-4.62 (m, 2H), 7.08 (br d, J=8.63 Hz, 2H), 7.41-7.47 (m, 2H), 7.47-7.51 (m, 1H), 7.57 (br d, J=6.38 Hz, 1H), 7.64 (br d, J=8.50 Hz, 1H), 7.69 (s, 1H), 12.57 (br s, 1H)

LCMS (ESI+): RT=2.751 min, m/z 461.0 (M+H)⁺.

5_95AB_6min-220-254-ELSD: LC/MS (The gradient was 5% B in 0.40 min and 5-95% B in 2.60 min, hold on 95% B in 1.00 min, and then 95-5% B in 0.01 min, the flow rate was 1.0 ml/min. Mobile phase A was 0.04% trifluoroacetic acid in water, mobile phase B was 0.02% trifluoroacetic acid in acetonitrile. The column used for chromatography was a Kinetex C18 2.1*50 mm, 5 um. Detection methods are diode array (DAD), and evaporative light scattering detection (ELSD). MS mode was positive electrospray ionization. MS range was 100-1000.

Synthesis of NUCC-0226243

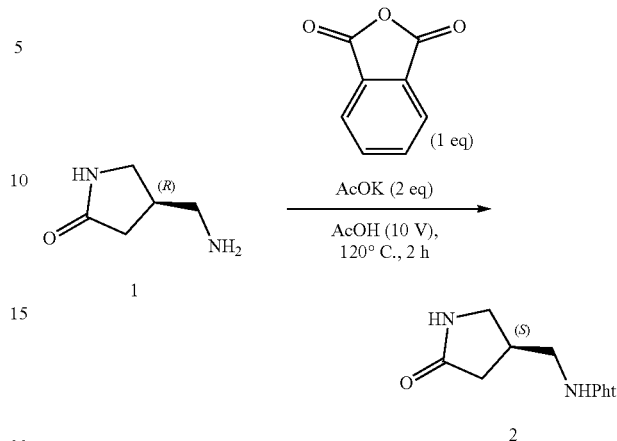

A mixture of Cpd 1 (1 g, 6.64 mmol), isobenzofuran-1,3-dione (983 mg, 6.64 mmol), potassium acetate (1.30 g, 13.3 mmol) in acetic acid (10 mL) was degassed and purged with N₂ for 3 times, and then the mixture was stirred at 120° C. for 12 hr under N₂ atmosphere. The reaction mixture was concentrated under reduced pressure to give a residue. The residue was purified by column chromatography on silica gel (dichloromethane:methanol=1:0 to 20:1) to give Cpd 2 (1 g, yield 55%) as white solid.

¹H NMR (400 MHz, CHLOROFORM-d)
δ 2.23 (dd, J=17.10, 7.02 Hz, 1H), 2.45-2.55 (m, 1H), 2.92-3.05 (m, 1H), 3.27 (dd, J=9.87, 5.70 Hz, 1H), 3.50 (dd, J=9.87, 7.89 Hz, 1H), 3.75-3.86 (m, 2H), 6.12 (br s, 1H), 7.73-7.78 (m, 2H), 7.87 (dd, J=5.48, 3.07 Hz, 2H)

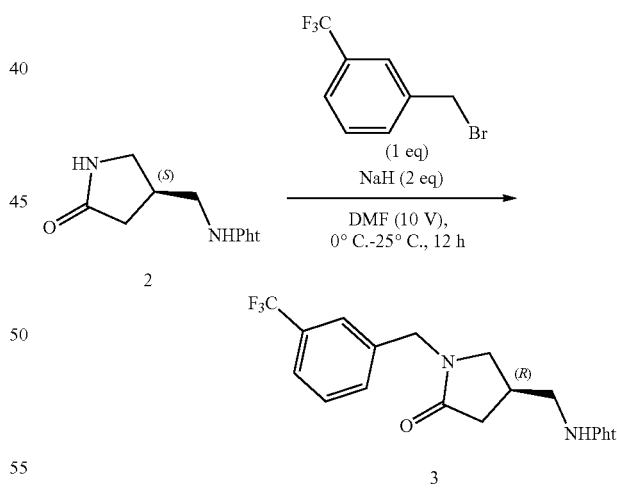

To a mixture of Cpd 2 (1 g, 4.09 mmol) in N,N-dimethylformamide (10 mL) was added NaH (327 mg, 8.19 mmol, 60% purity) at 0° C. The reaction mixture was stirred at 0° C. for 0.5 h. Then to the reaction mixture was added 1-(bromomethyl)-3-(trifluoromethyl)benzene (978 mg, 4.09 mmol) at 0° C., the reaction mixture was stirred 25° C. for 12 hr under N₂ atmosphere. The reaction mixture was quenched by addition ammonium chloride (50 mL), and then extracted with ethyl acetate (50 mL×2). The combined organic layers were washed with aqueous NaCl (50 mL)

dried over Na₂SO₄, filtered and concentrated under reduced pressure to give a residue. The residue was purified by column chromatography on silica gel (petroleum ether:ethyl acetate=1:0 to 20:1) to give Cpd 3 (600 mg, yield 32%) as white solid ¹H NMR (400 MHz, CHLOROFORM-d)

δ 2.34 (dd, J=16.99, 6.85 Hz, 1H), 2.56-2.68 (m, 1H), 2.79-2.87 (m, 1H), 3.15 (dd, J=9.90, 5.75 Hz, 1H), 3.34 (dd, J=9.78, 8.07 Hz, 1H), 3.74 (d, J=7.34 Hz, 2H), 4.33 (d, J=14.92 Hz, 1H), 4.67 (d, J=14.92 Hz, 1H), 7.41-7.49 (m, 2H), 7.54 (br d, J=6.72 Hz, 1H), 7.71-7.78 (m, 2H), 7.81-7.88 (m, 2H)

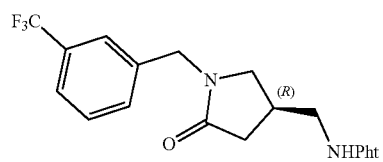

3

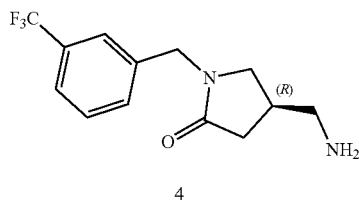

4

To a mixture of Cpd 3 (500 mg, 1.24 mmol) in ethanol (15 mL) was added NH₂NH₂·H₂O (109.78 mg, 1.86 mmol, 85% purity) at 25° C., the reaction mixture was stirred 80° C. for 12 hr under N₂ atmosphere. The reaction mixture was filtered and concentrated under reduced pressure to give a residue. The residue was purified by Prep-HPLC to give Cpd 4 (120 mg, yield 35%) as a colorless oil.

Prep-HPLC Methods:

Instrument: Gilson 281 semi-preparative HPLC system

Mobile phase: A: TFA/H2O=0.075% v/v; B: acetonitrile

Column: Phenomenex luna C18 100×40mm×5 um

Flow rate: 25 mL/min

Monitor wavelength: 220&254 nm

Time B %

0.0 10

8.0 40

8.1 40

8.2 100

11.2 100

11.3 10

12.5 10

¹H NMR (400 MHz, CHLOROFORM-d)

δ 2.48-2.60 (m, 1H), 2.74-2.90 (m, 2H), 2.96-3.18 (m, 4H), 3.49-3.58 (m, 1H), 4.40 (d, J=14.77 Hz, 1H), 4.52-4.61 (m, 1H), 7.36-7.41 (m, 1H), 7.42-7.50 (m, 2H), 7.57 (d, J=7.72 Hz, 1H)

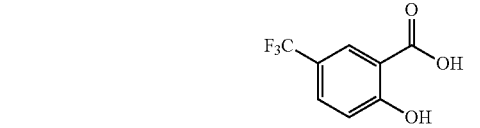

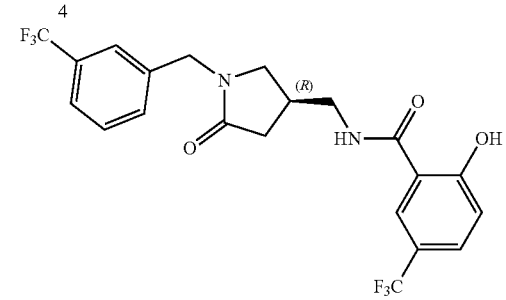

NUCC-0226243

To a mixture of 2-hydroxy-5-(trifluoromethyl)benzoic acid (75.7 mg, 367 umol) in N,N-dimethylformamide (1 mL) was added O-(7-azabenzotriazol-1-yl)-N,N,N',N'-tetramethyluronium hexafluorophosphate (167 mg, 440 umol) and N-ethyl-N-isopropylpropan-2-amine (142 mg, 1.10 mmol) at 25° C., the reaction mixture was stirred at 25° C. for 5 min, then to the reaction mixture was added Cpd 4 (100 mg, 367 umol) and the reaction was stirred at 25° C. for 12 hr. The reaction mixture was quenched by addition water (10 mL), and then extracted with ethyl acetate (10 mL×2). The combined organic layers were washed with aqueous NaCl (10 mL) dried over Na₂SO₄, filtered and concentrated under reduced pressure to give a residue which was purified by Prep-HPLC to give P4-001 (20 mg, 20% yield) as white solid Prep-HPLC methods:

Instrument: Gilson 281 semi-preparative HPLC system

Mobile phase: A: TFA/H2O=0.075% v/v; B: acetonitrile

Column: Phenomenex Luna C18 150×30 mm×5 um

Flow rate: 25 mL/min

Monitor wavelength: 220&254 nm

Time B %

0.0 43

8.0 73

8.1 73

8.2 100

10.2 100

10.3 43

11.5 43

¹H NMR 400 MHz, DMSO-d6)

δ 2.22 (dd, J=16.75, 5.99 Hz, 1H), 2.51-2.55 (m, 1H), 2.61-2.71 (m, 1H), 3.07 (dd, J=9.90, 5.14 Hz, 1H), 3.29-3.43 (m, 3H), 4.46 (s, 2H), 7.09 (d, J=8.68 Hz, 1H), 7.50-7.60 (m, 3H), 7.61-7.65 (m, 1H), 7.73 (dd, J=8.68, 1.83 Hz, 1H), 8.20 (d, J=1.22 Hz, 1H), 9.06 (br t, J=5.56 Hz, 1H), 13.00 (br s, 1H)

LCMS (ESI+): RT=2.729 min, m/z 461.1 (M+H)⁺.

Method of LCMS:

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50×2.1mm column (5 um particles). Detection methods are diode array (DAD) and evaporative light scattering (ELSD) detection as well as positive electrospray ionization. MS range was 100-1000.
Synthesis of NUCC-0226236
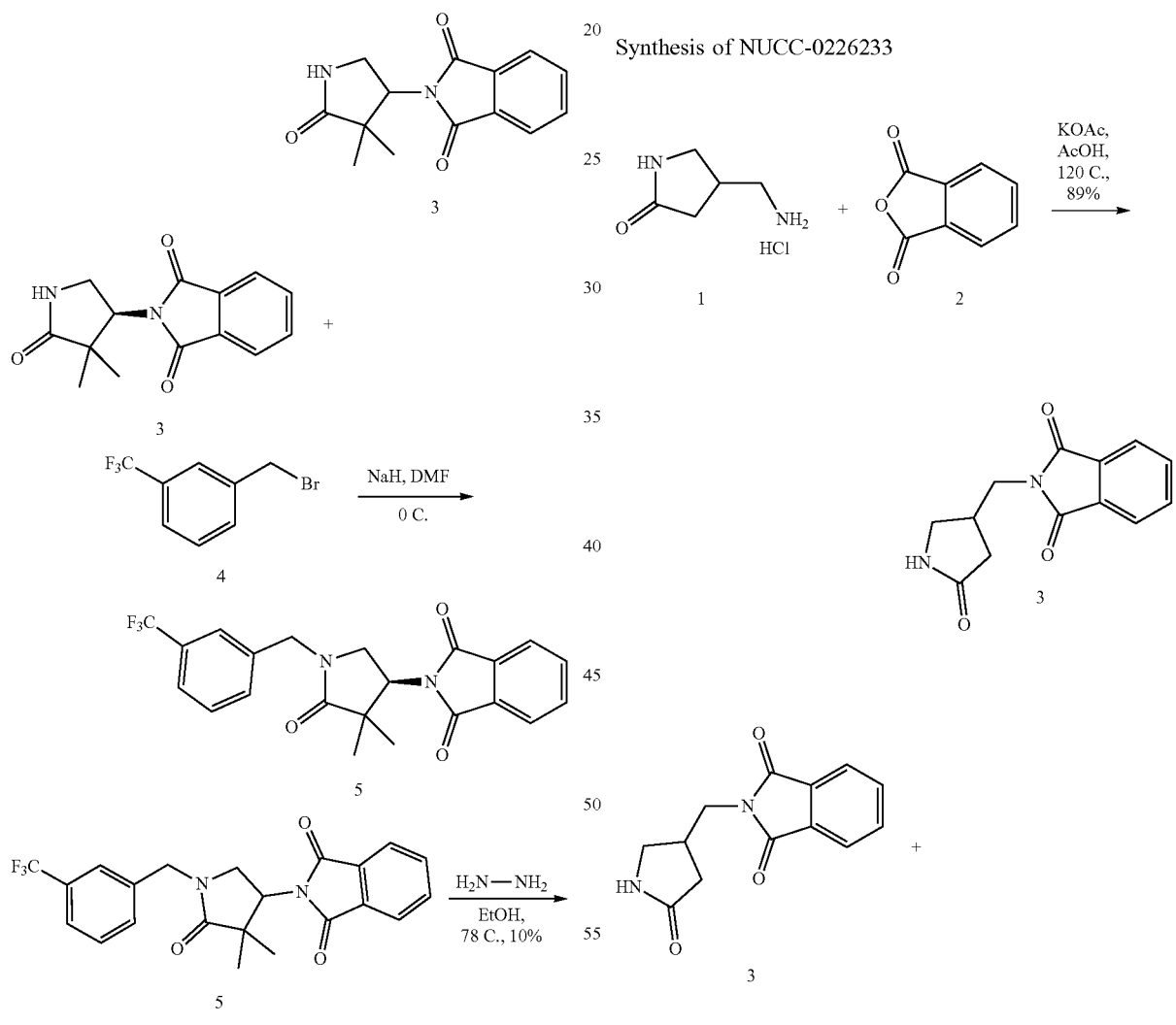
Synthesis of NUCC-0226233
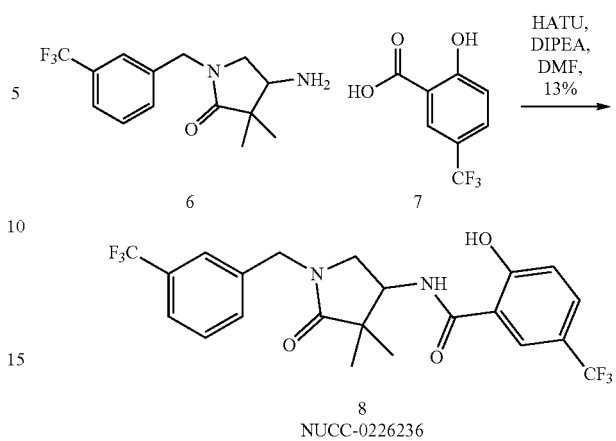
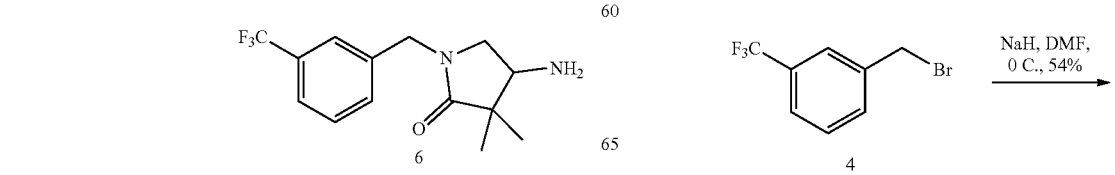

27
-continued
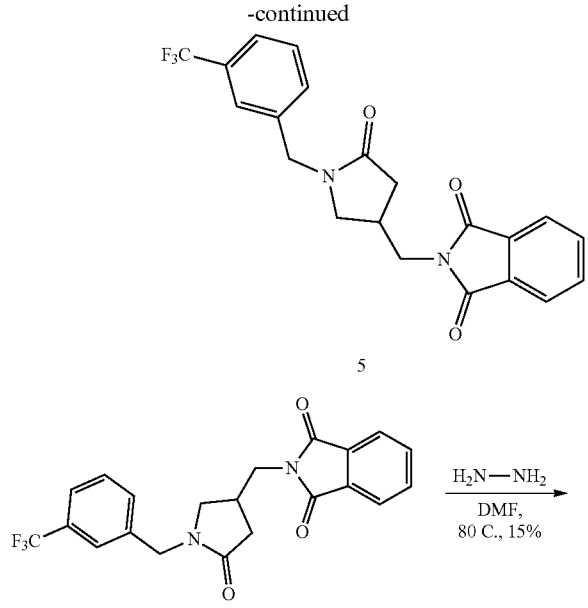
Synthesis of NUCC-0223821
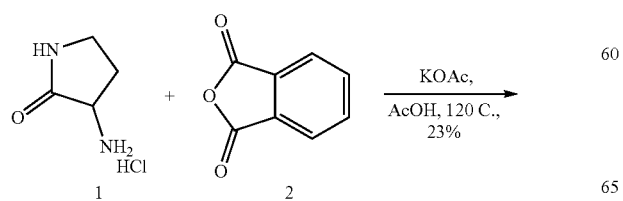
28
-continued
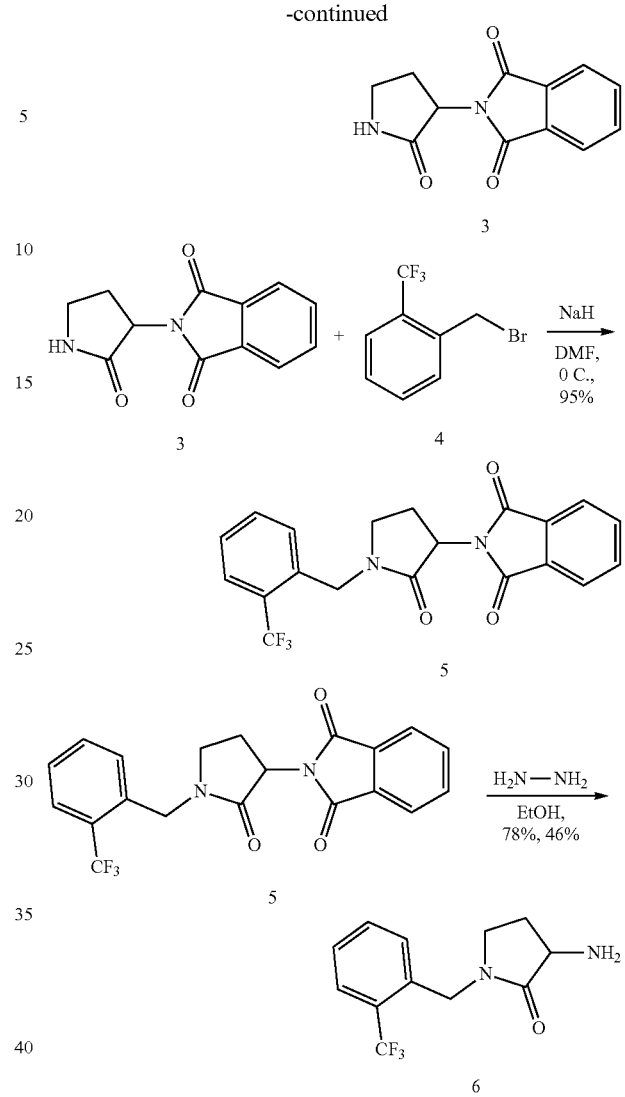
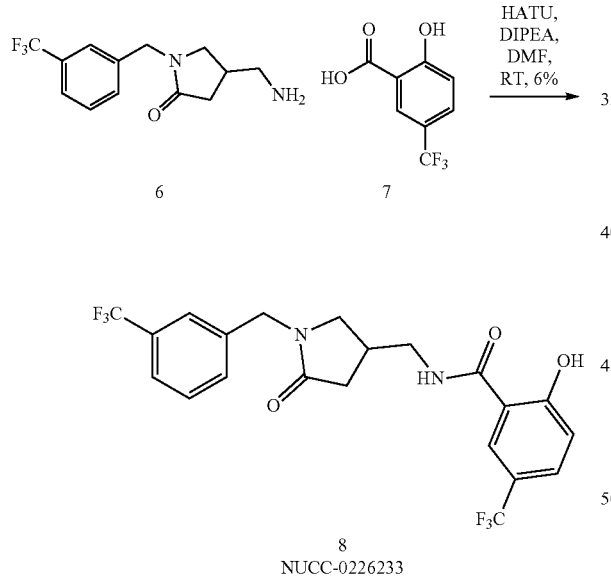
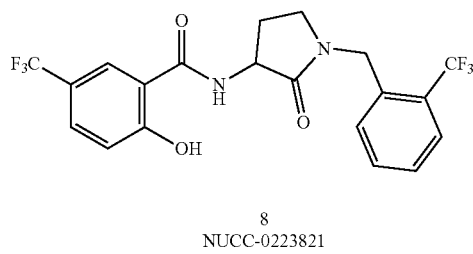

Synthesis of NUCC-0223628
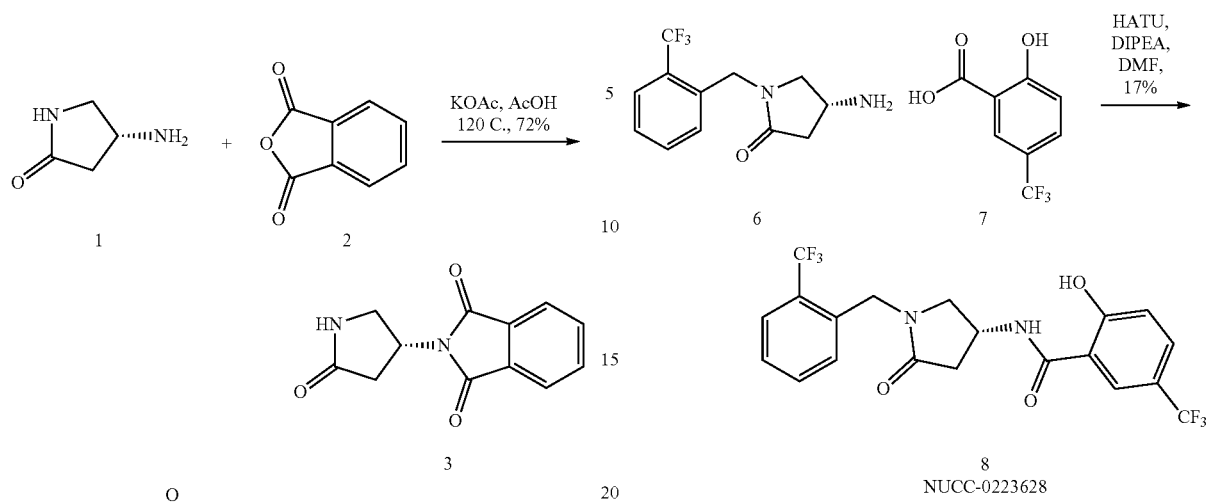
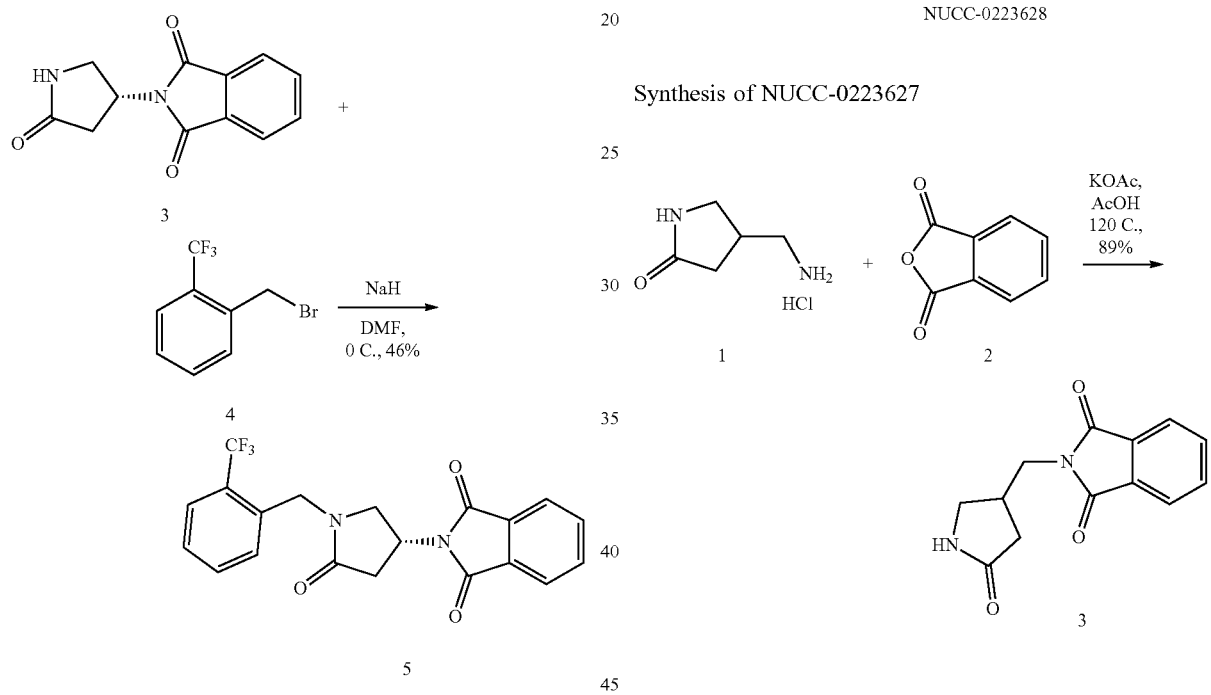
Synthesis of NUCC-0223627
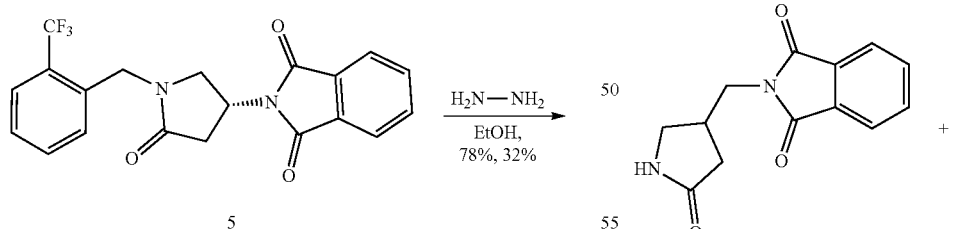
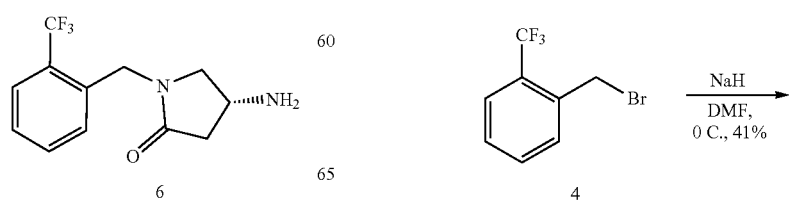

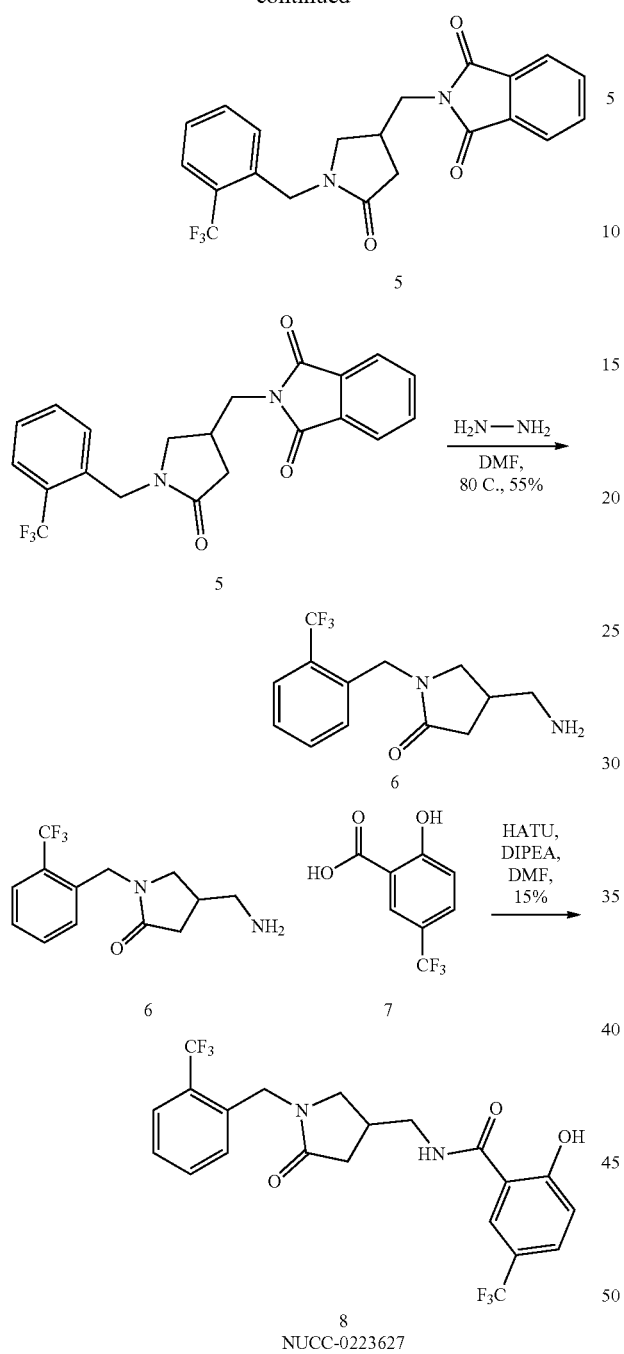
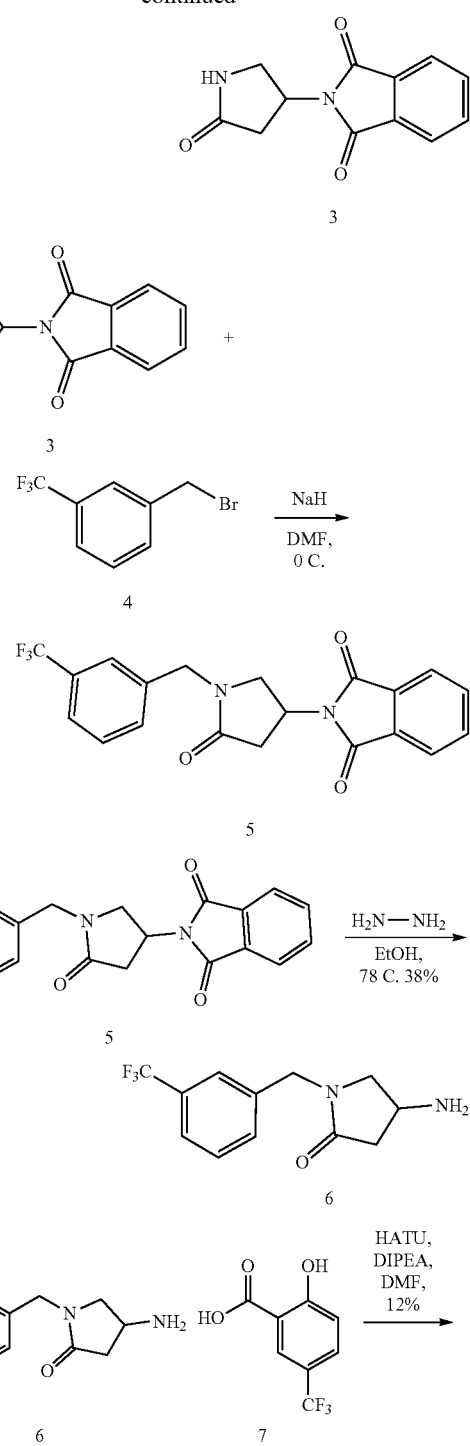
Synthesis of NUCC-0223625
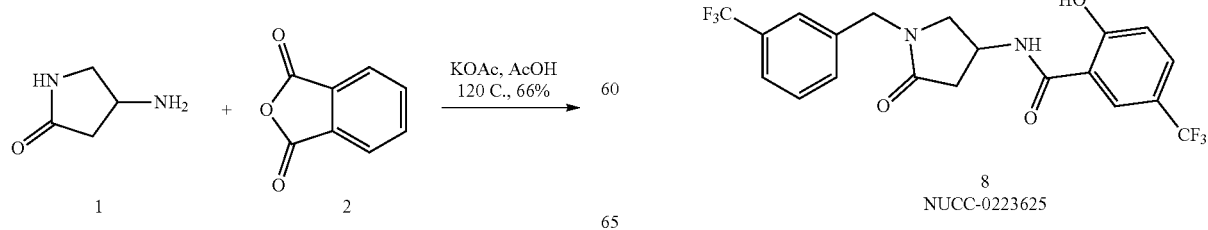

Synthesis of NUCC-0223624

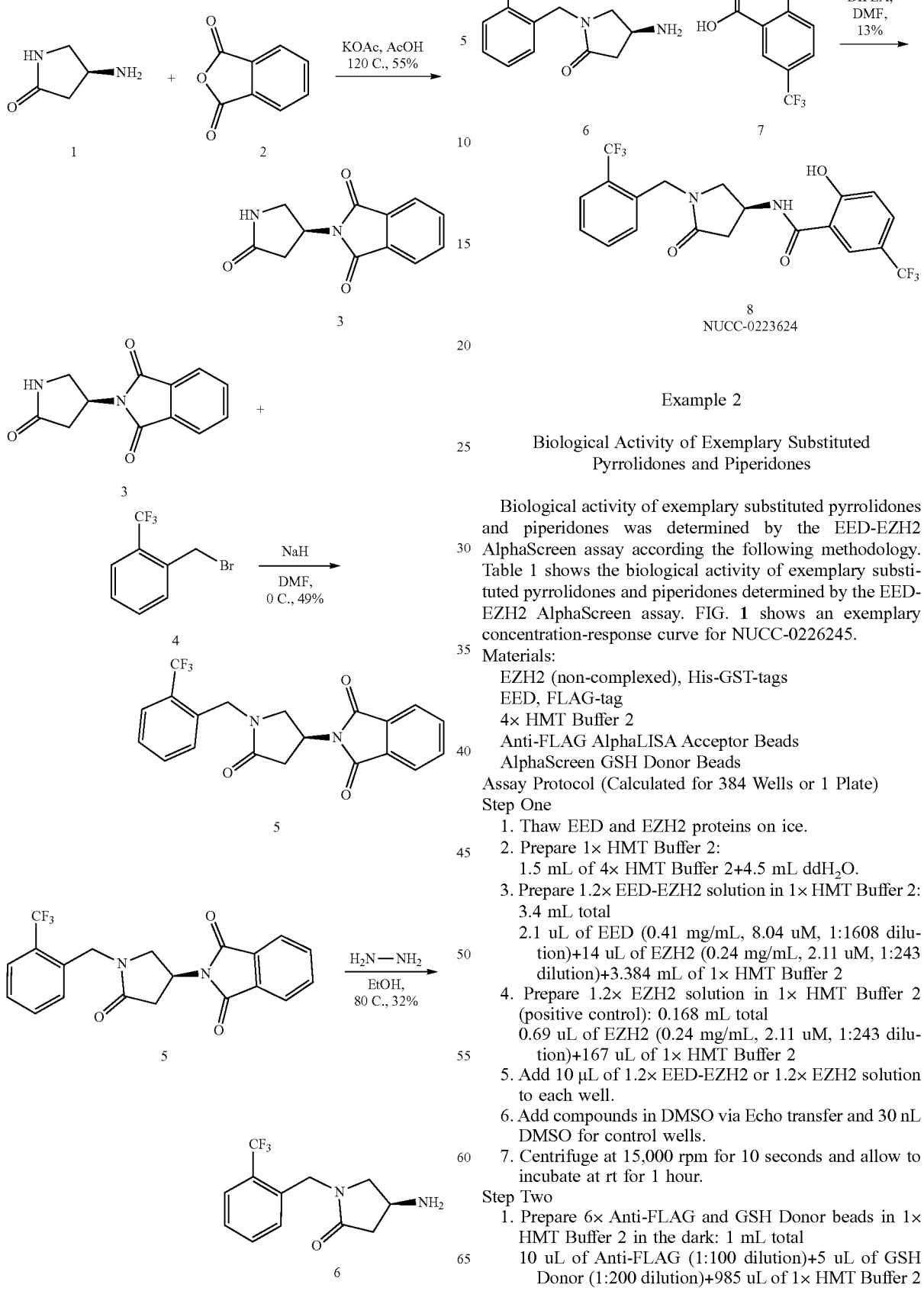

Example 2

Biological Activity of Exemplary Substituted Pyrrolidones and Piperidones

Biological activity of exemplary substituted pyrrolidones and piperidones was determined by the EED-EZH2 AlphaScreen assay according the following methodology. Table 1 shows the biological activity of exemplary substituted pyrrolidones and piperidones determined by the EED-EZH2 AlphaScreen assay. FIG. 1 shows an exemplary concentration-response curve for NUCC-0226245.

Materials:
  EZH2 (non-complexed), His-GST-tags
  EED, FLAG-tag
  4× HMT Buffer 2
  Anti-FLAG AlphaLISA Acceptor Beads
  AlphaScreen GSH Donor Beads Assay Protocol (Calculated for 384 Wells or 1 Plate)

Step One
  1. Thaw EED and EZH2 proteins on ice.
  2. Prepare 1× HMT Buffer 2:
     1.5 mL of 4× HMT Buffer 2+4.5 mL ddH$_2$O.
  3. Prepare 1.2× EED-EZH2 solution in 1× HMT Buffer 2: 3.4 mL total
     2.1 uL of EED (0.41 mg/mL, 8.04 uM, 1:1608 dilution)+14 uL of EZH2 (0.24 mg/mL, 2.11 uM, 1:243 dilution)+3.384 mL of 1× HMT Buffer 2
  4. Prepare 1.2× EZH2 solution in 1× HMT Buffer 2 (positive control): 0.168 mL total
     0.69 uL of EZH2 (0.24 mg/mL, 2.11 uM, 1:243 dilution)+167 uL of 1× HMT Buffer 2
  5. Add 10 µL of 1.2× EED-EZH2 or 1.2× EZH2 solution to each well.
  6. Add compounds in DMSO via Echo transfer and 30 nL DMSO for control wells.
  7. Centrifuge at 15,000 rpm for 10 seconds and allow to incubate at rt for 1 hour.

Step Two
  1. Prepare 6× Anti-FLAG and GSH Donor beads in 1× HMT Buffer 2 in the dark: 1 mL total
     10 uL of Anti-FLAG (1:100 dilution)+5 uL of GSH Donor (1:200 dilution)+985 uL of 1× HMT Buffer 2
  2. Add 2 µL of bead solution to each well.

3. Centrifuge at 15,000 rpm for 10 seconds and allow to incubate at rt for 1 hour in the dark.
4. Read plate.

Final Concentrations:
12 µL volume per well
8.7 nM EZH2
5.0 nM EED
DMSO<0.5%

Calculations:
1. Average EZH2 only wells (positive control) and subtract from all other wells.
2. Average EED-EZH2 only wells (negative control) to indicate 100% signal or 0% inhibition.
3. Normalize each well to the average 100% signal from step 2.
4. Report either as normalized % inhibition or normalized % signal.

Use GraphPad to Calculate $IC_{50}$.

TABLE 1

Representative Compounds and Biological Activity

IC50 Potency Code:
<1 µM: ***
1-10 µM: **
10-50 µM: *
>50 µM: /

| Molecule Name | Structure | |
|---|---|---|
| NUCC-0163358 | 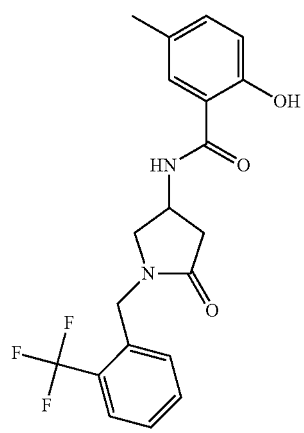 [SMILES: Cc1ccc(O)c(C(=O)NC2CC(=O)N(Cc3ccccc3C(F)(F)F)C2)c1] | ** |
| NUCC-0202653 | 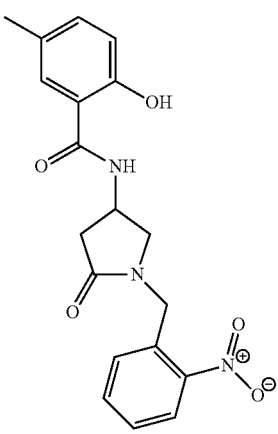 [SMILES: Cc1ccc(O)c(C(=O)NC2CC(=O)N(Cc3ccccc3[N+](=O)[O-])C2)c1] | ** |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202654 | 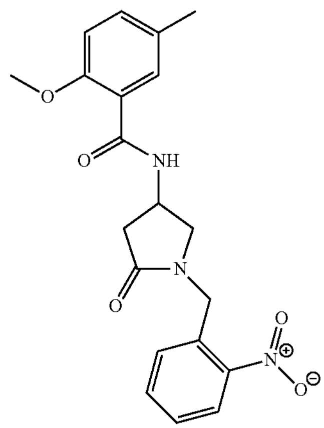 [SMILES: COc1ccc(C)cc1C(=O)NC1CC(=O)N(Cc2ccccc2[N+](=O)[O-])C1] | / |
| NUCC-0202655 | 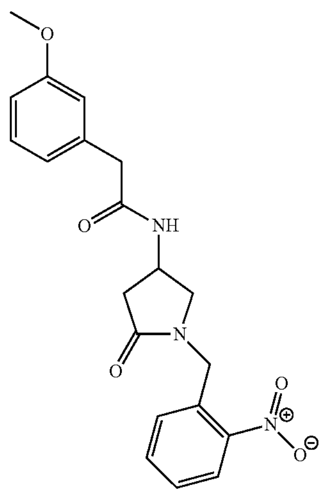 [SMILES: COc1cccc(CC(=O)NC2CC(=O)N(Cc3ccccc3[N+](=O)[O-])C2)c1] | / |
| NUCC-0202656 | 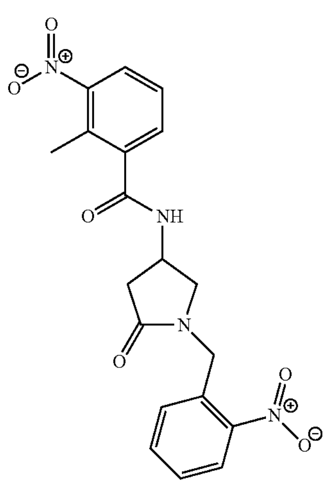 [SMILES: Cc1c(C(=O)NC2CC(=O)N(Cc3ccccc3[N+](=O)[O-])C2)cccc1[N+](=O)[O-]] | / |

TABLE 1-continued
Representative Compounds and Biological Activity
| Molecule Name | Structure | IC50 Potency Code:<br><1 μM: ***<br>1-10 μM: **<br>10-50 μM: *<br>>50 μM: / |
|---|---|---|
| NUCC-0202657 | 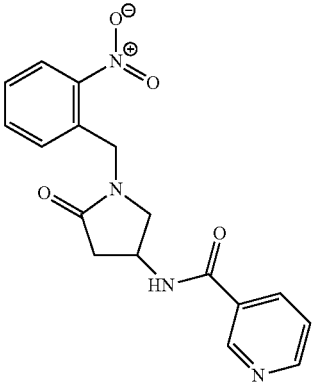 [SMILES: O=C(NC1CC(=O)N(Cc2ccccc2[N+](=O)[O-])C1)c1cccnc1] | / |
| NUCC-0202658 | 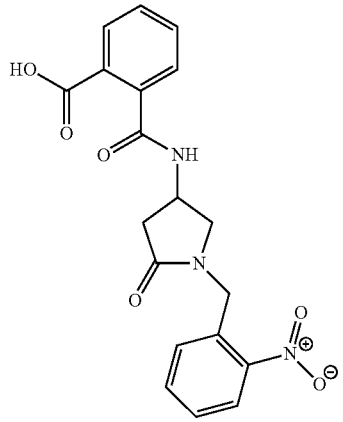 [SMILES: O=C(O)c1ccccc1C(=O)NC1CC(=O)N(Cc2ccccc2[N+](=O)[O-])C1] | / |
| NUCC-0202659 | 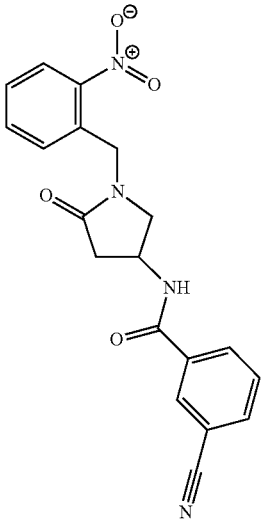 [SMILES: N#Cc1cccc(C(=O)NC2CC(=O)N(Cc3ccccc3[N+](=O)[O-])C2)c1] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202660 | 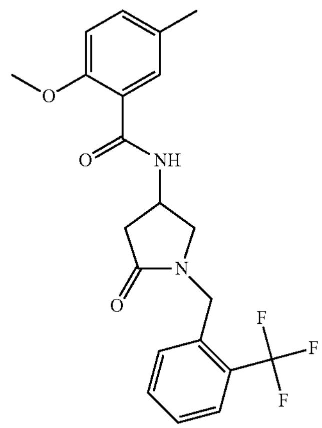 [SMILES: COc1ccc(C)cc1C(=O)NC1CC(=O)N(Cc2ccccc2C(F)(F)F)C1] | * |
| NUCC-0202661 | 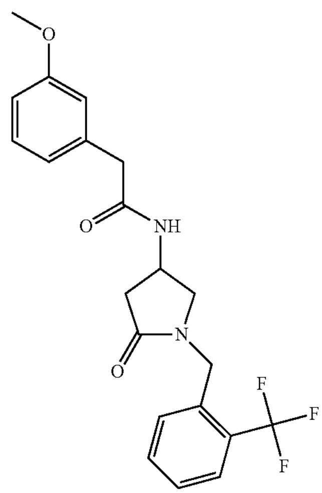 [SMILES: COc1cccc(CC(=O)NC2CC(=O)N(Cc3ccccc3C(F)(F)F)C2)c1] | / |
| NUCC-0202662 | 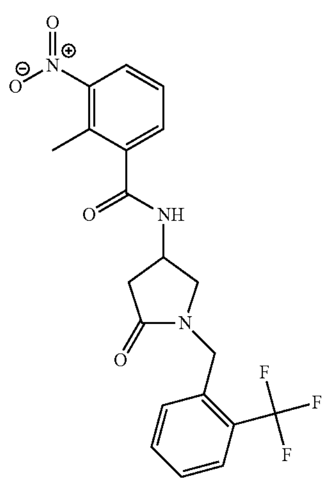 [SMILES: Cc1c(C(=O)NC2CC(=O)N(Cc3ccccc3C(F)(F)F)C2)cccc1[N+](=O)[O-]] | / |

TABLE 1-continued
Representative Compounds and Biological Activity
| Molecule Name | Structure | IC50 Potency Code:<br><1 μM: ***<br>1-10 μM: **<br>10-50 μM: *<br>>50 μM: / |
|---|---|---|
| NUCC-0202663 | 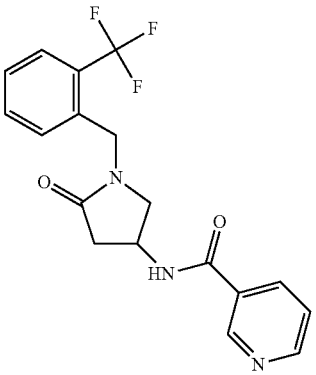 [SMILES: O=C(NC1CC(=O)N(Cc2ccccc2C(F)(F)F)C1)c1cccnc1] | / |
| NUCC-0202666 | 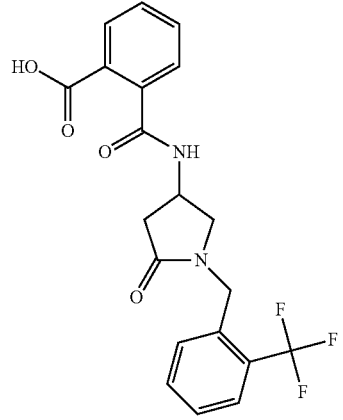 [SMILES: O=C(O)c1ccccc1C(=O)NC1CC(=O)N(Cc2ccccc2C(F)(F)F)C1] | / |
| NUCC-0202667 | 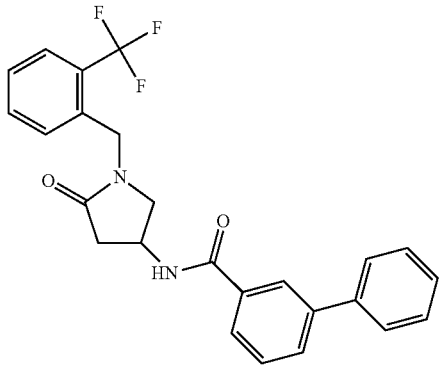 [SMILES: O=C(NC1CC(=O)N(Cc2ccccc2C(F)(F)F)C1)c1cccc(-c2ccccc2)c1] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202668 | 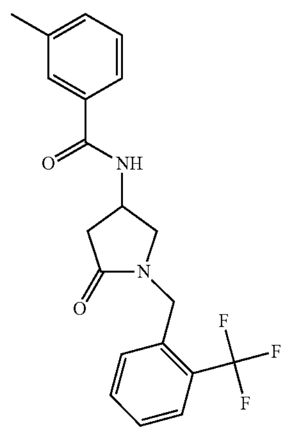 [SMILES: Cc1cccc(C(=O)NC2CC(=O)N(Cc3ccccc3C(F)(F)F)C2)c1] | / |
| NUCC-0202669 | 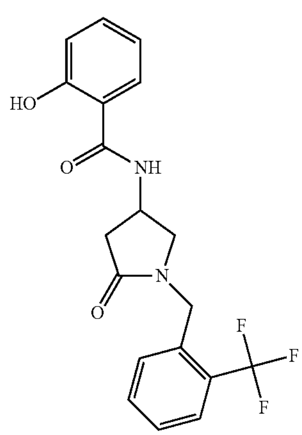 [SMILES: O=C(NC1CC(=O)N(Cc2ccccc2C(F)(F)F)C1)c1ccccc1O] | / |
| NUCC-0202670 | 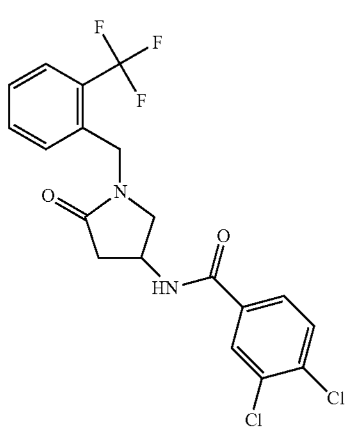 [SMILES: O=C(NC1CC(=O)N(Cc2ccccc2C(F)(F)F)C1)c1ccc(Cl)c(Cl)c1] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202671 | 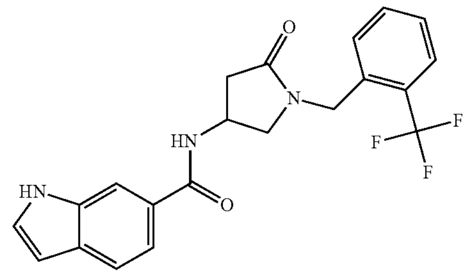 [SMILES: O=C(NC1CC(=O)N(Cc2ccccc2C(F)(F)F)C1)c1ccc2cc[nH]c2c1] | / |
| NUCC-0202672 | 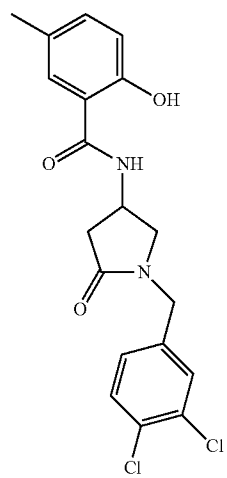 [SMILES: Cc1ccc(O)c(C(=O)NC2CC(=O)N(Cc3ccc(Cl)c(Cl)c3)C2)c1] | * |
| NUCC-0202673 | 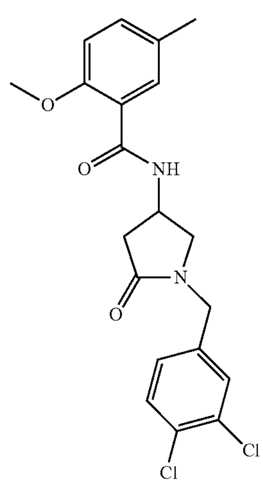 [SMILES: COc1ccc(C)cc1C(=O)NC1CC(=O)N(Cc2ccc(Cl)c(Cl)c2)C1] | / |

TABLE 1-continued
Representative Compounds and Biological Activity
| Molecule Name | Structure | IC50 Potency Code:<br><1 μM: ***<br>1-10 μM: **<br>10-50 μM: *<br>>50 μM: / |
|---|---|---|
| NUCC-0202674 | 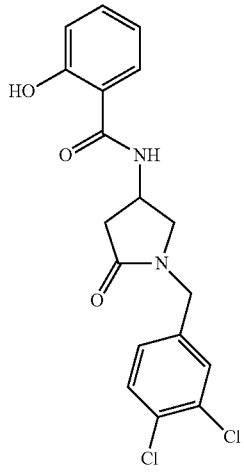 [SMILES: O=C(NC1CC(=O)N(Cc2ccc(Cl)c(Cl)c2)C1)c1ccccc1O] | / |
| NUCC-0202675 | 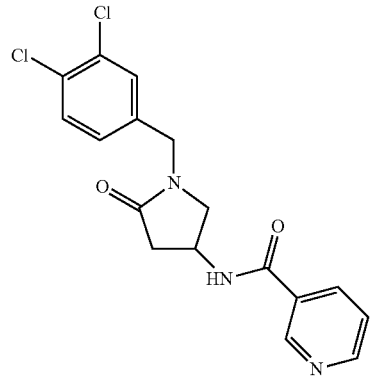 [SMILES: O=C(NC1CC(=O)N(Cc2ccc(Cl)c(Cl)c2)C1)c1cccnc1] | / |
| NUCC-0202676 | 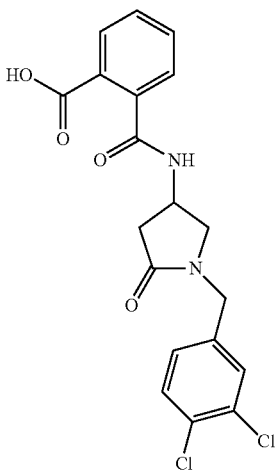 [SMILES: O=C(O)c1ccccc1C(=O)NC1CC(=O)N(Cc2ccc(Cl)c(Cl)c2)C1] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202677 | 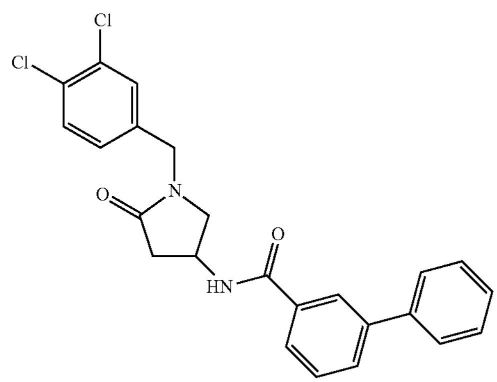 [SMILES: O=C(NC1CC(=O)N(Cc2ccc(Cl)c(Cl)c2)C1)c1cccc(-c2ccccc2)c1] | / |
| NUCC-0202678 | 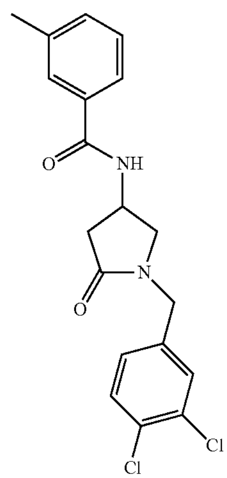 [SMILES: Cc1cccc(C(=O)NC2CC(=O)N(Cc3ccc(Cl)c(Cl)c3)C2)c1] | / |
| NUCC-0202747 | 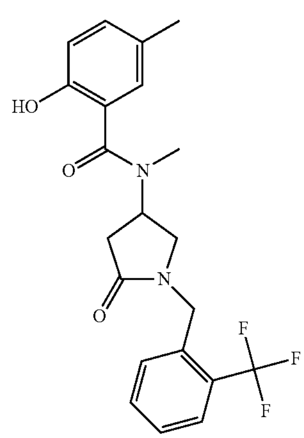 [SMILES: Cc1ccc(O)c(C(=O)N(C)C2CC(=O)N(Cc3ccccc3C(F)(F)F)C2)c1] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202749 | 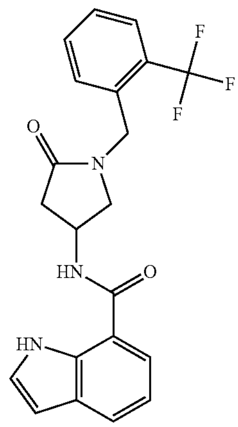 [SMILES: O=C(NC1CC(=O)N(Cc2ccccc2C(F)(F)F)C1)c1cccc2cc[nH]c12] | / |
| NUCC-0202750 | 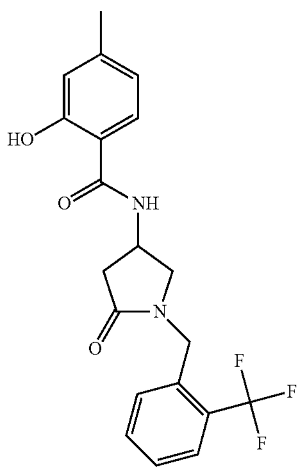 [SMILES: Cc1ccc(C(=O)NC2CC(=O)N(Cc3ccccc3C(F)(F)F)C2)c(O)c1] | / |
| NUCC-0202751 | 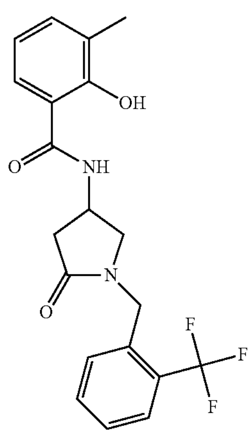 [SMILES: Cc1cccc(C(=O)NC2CC(=O)N(Cc3ccccc3C(F)(F)F)C2)c1O] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202752 | 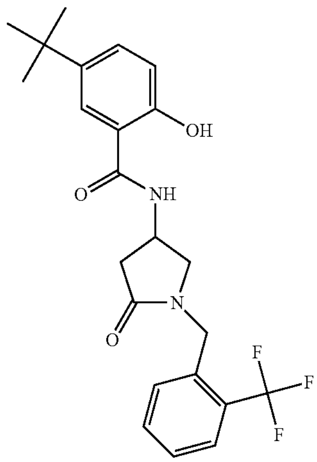 [SMILES: CC(C)(C)c1ccc(O)c(C(=O)NC2CC(=O)N(Cc3ccccc3C(F)(F)F)C2)c1] | / |
| NUCC-0202753 | 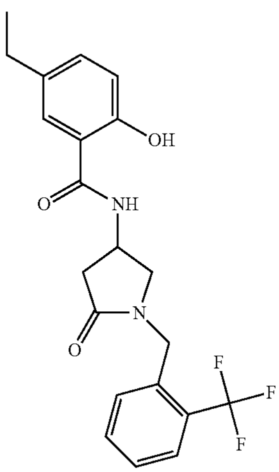 [SMILES: CCc1ccc(O)c(C(=O)NC2CC(=O)N(Cc3ccccc3C(F)(F)F)C2)c1] | / |
| NUCC-0202754 | 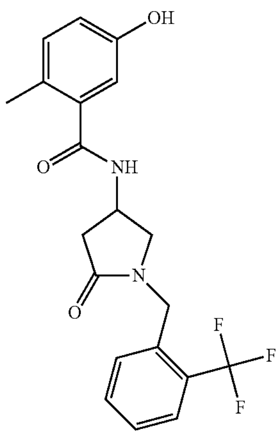 [SMILES: Cc1ccc(O)cc1C(=O)NC1CC(=O)N(Cc2ccccc2C(F)(F)F)C1] | / |

TABLE 1-continued

Representative Compounds and Biological Activity

| Molecule Name | Structure | IC50 Potency Code:<br><1 µM: ***<br>1-10 µM: **<br>10-50 µM: *<br>>50 µM: / |
|---|---|---|
| NUCC-0202755 | 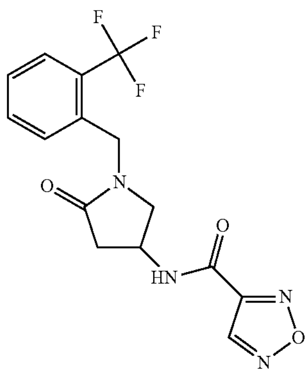 [SMILES: O=C(NC1CC(=O)N(Cc2ccccc2C(F)(F)F)C1)c1cnon1] | / |
| NUCC-0202756 | 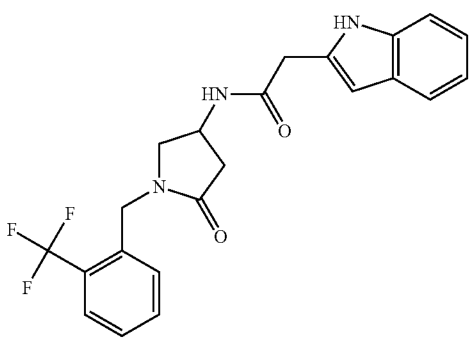 [SMILES: O=C(Cc1cc2ccccc2[nH]1)NC1CC(=O)N(Cc2ccccc2C(F)(F)F)C1] | / |
| NUCC-0202757 | 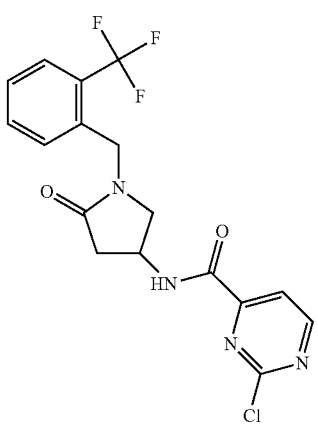 [SMILES: O=C(NC1CC(=O)N(Cc2ccccc2C(F)(F)F)C1)c1ccnc(Cl)n1] | / |
| NUCC-0202758 | 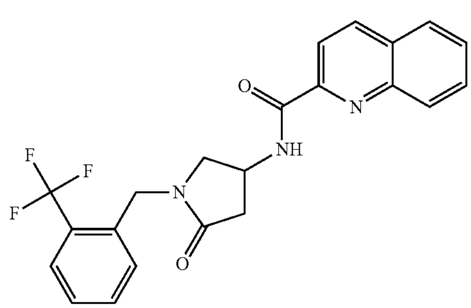 [SMILES: O=C(NC1CC(=O)N(Cc2ccccc2C(F)(F)F)C1)c1ccc2ccccc2n1] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202759 | 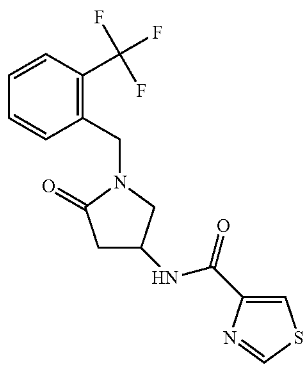 [SMILES: O=C(NC1CC(=O)N(Cc2ccccc2C(F)(F)F)C1)c1cscn1] | / |
| NUCC-0202760 | 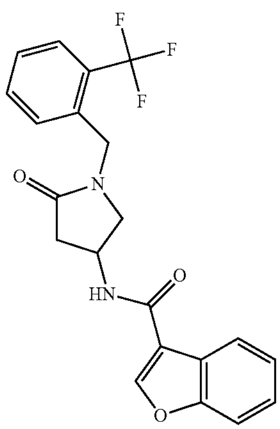 [SMILES: O=C(NC1CC(=O)N(Cc2ccccc2C(F)(F)F)C1)c1coc2ccccc12] | / |
| NUCC-0202761 | 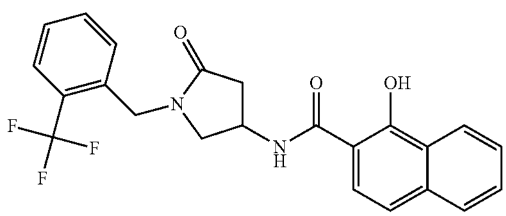 [SMILES: O=C(NC1CC(=O)N(Cc2ccccc2C(F)(F)F)C1)c1ccc2ccccc2c1O] | * |
| NUCC-0202762 | 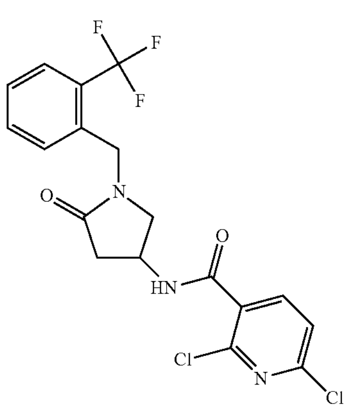 [SMILES: O=C(NC1CC(=O)N(Cc2ccccc2C(F)(F)F)C1)c1ccc(Cl)nc1Cl] | / |

TABLE 1-continued
Representative Compounds and Biological Activity
| Molecule Name | Structure | IC50 Potency Code:<br><1 μM: ***<br>1-10 μM: **<br>10-50 μM: *<br>>50 μM: / |
|---|---|---|
| NUCC-0202763 | 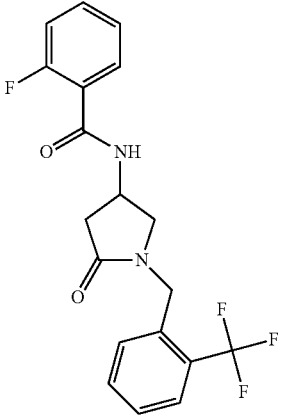 [SMILES: O=C(NC1CC(=O)N(Cc2ccccc2C(F)(F)F)C1)c1ccccc1F] | / |
| NUCC-0202764 | 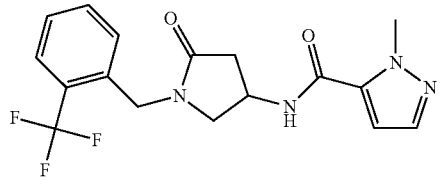 [SMILES: Cn1nccc1C(=O)NC1CC(=O)N(Cc2ccccc2C(F)(F)F)C1] | / |
| NUCC-0202765 | 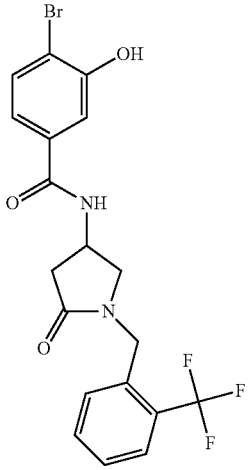 [SMILES: O=C(NC1CC(=O)N(Cc2ccccc2C(F)(F)F)C1)c1ccc(Br)c(O)c1] | / |
| NUCC-0202766 | 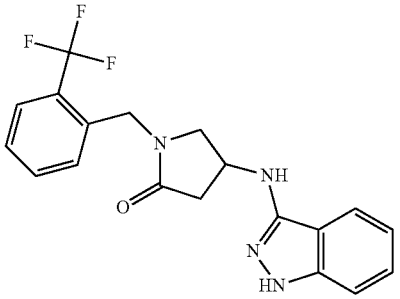 [SMILES: O=C1CC(Nc2n[nH]c3ccccc23)CN1Cc1ccccc1C(F)(F)F] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202792 | 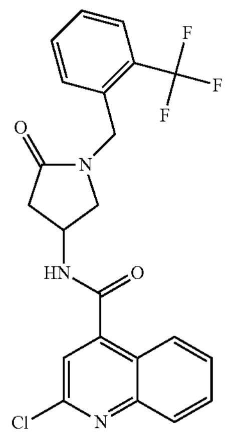 [SMILES: O=C(NC1CC(=O)N(Cc2ccccc2C(F)(F)F)C1)c1cc(Cl)nc2ccccc12] | / |
| NUCC-0202793 | 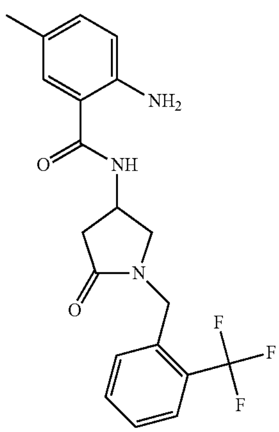 [SMILES: Cc1ccc(N)c(C(=O)NC2CC(=O)N(Cc3ccccc3C(F)(F)F)C2)c1] | / |
| NUCC-0202826 | 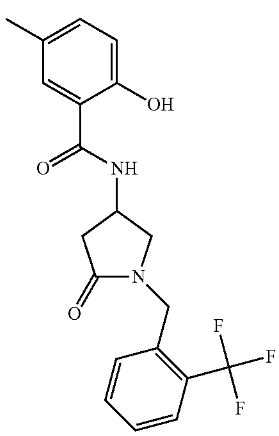 [SMILES: Cc1ccc(O)c(C(=O)NC2CC(=O)N(Cc3ccccc3C(F)(F)F)C2)c1] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202827 | 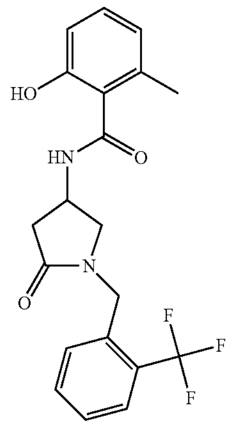 [SMILES: Cc1cccc(O)c1C(=O)NC1CC(=O)N(Cc2ccccc2C(F)(F)F)C1] | / |
| NUCC-0202828 | 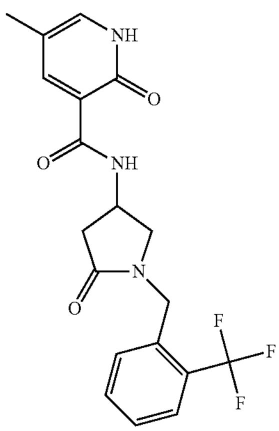 [SMILES: Cc1c[nH]c(=O)c(C(=O)NC2CC(=O)N(Cc3ccccc3C(F)(F)F)C2)c1] | / |
| NUCC-0202830 | 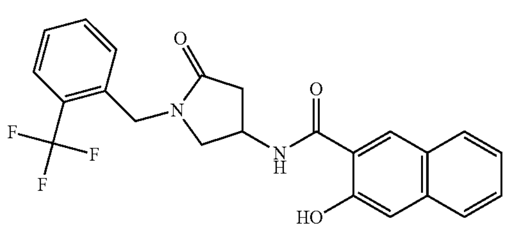 [SMILES: O=C(NC1CC(=O)N(Cc2ccccc2C(F)(F)F)C1)c1cc2ccccc2cc1O] | * |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202831 | 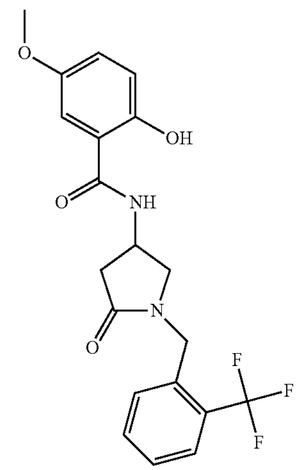 [SMILES: COc1ccc(O)c(C(=O)NC2CC(=O)N(Cc3ccccc3C(F)(F)F)C2)c1] | * |
| NUCC-0202832 | 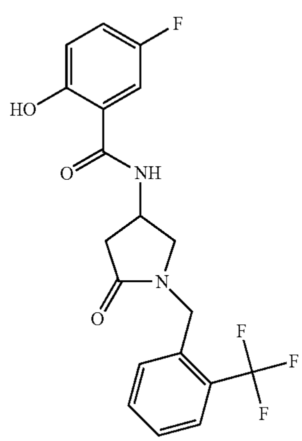 [SMILES: O=C(NC1CC(=O)N(Cc2ccccc2C(F)(F)F)C1)c1cc(F)ccc1O] | ** |
| NUCC-0202833 | 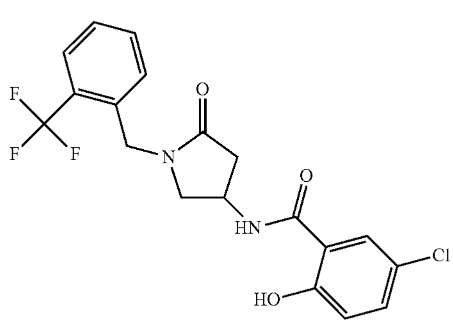 [SMILES: O=C(NC1CC(=O)N(Cc2ccccc2C(F)(F)F)C1)c1cc(Cl)ccc1O] | ** |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202834 | 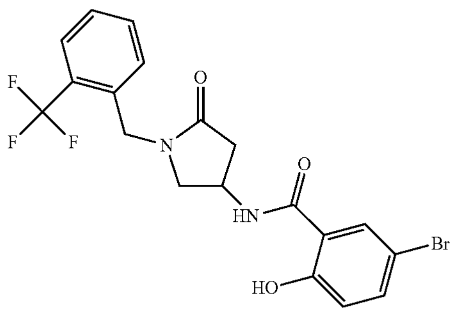 [SMILES: O=C(NC1CC(=O)N(Cc2ccccc2C(F)(F)F)C1)c1cc(Br)ccc1O] | ** |
| NUCC-0202835 | 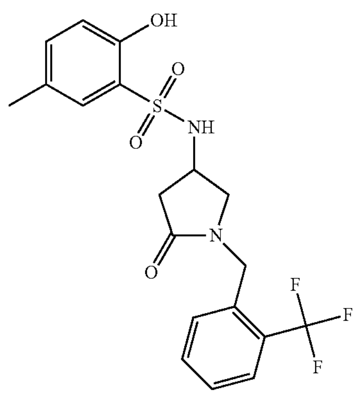 [SMILES: Cc1ccc(O)c(S(=O)(=O)NC2CC(=O)N(Cc3ccccc3C(F)(F)F)C2)c1] | / |
| NUCC-0202850 | 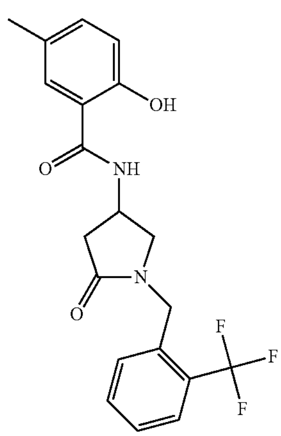 [SMILES: Cc1ccc(O)c(C(=O)NC2CC(=O)N(Cc3ccccc3C(F)(F)F)C2)c1] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202851 | 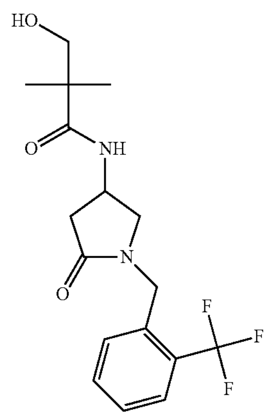 [SMILES: CC(C)(CO)C(=O)NC1CC(=O)N(Cc2ccccc2C(F)(F)F)C1] | / |
| NUCC-0202852 | 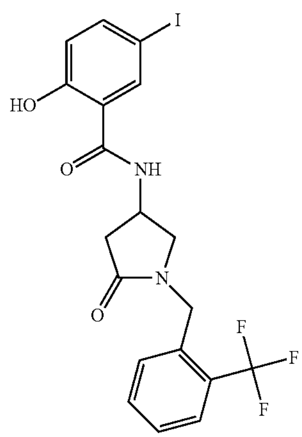 [SMILES: O=C(NC1CC(=O)N(Cc2ccccc2C(F)(F)F)C1)c1cc(I)ccc1O] | * |
| NUCC-0202965 | 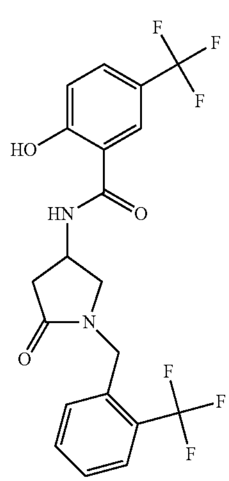 [SMILES: O=C(NC1CC(=O)N(Cc2ccccc2C(F)(F)F)C1)c1cc(C(F)(F)F)ccc1O] | ** |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202966 | 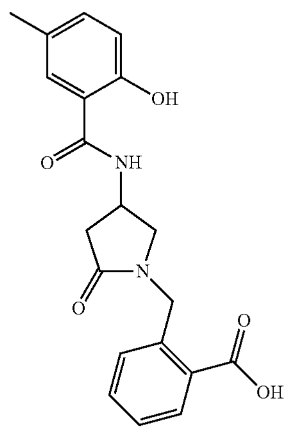 [SMILES: Cc1ccc(O)c(C(=O)NC2CC(=O)N(Cc3ccccc3C(=O)O)C2)c1] | ** |
| NUCC-0202967 | 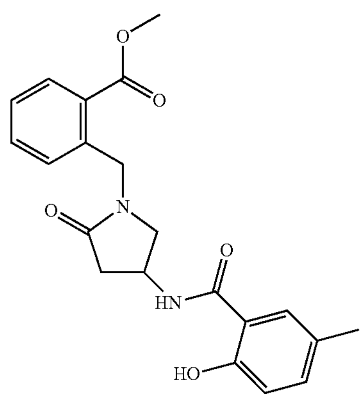 [SMILES: COC(=O)c1ccccc1CN1CC(NC(=O)c2cc(C)ccc2O)CC1=O] | ** |
| NUCC-0202968 | 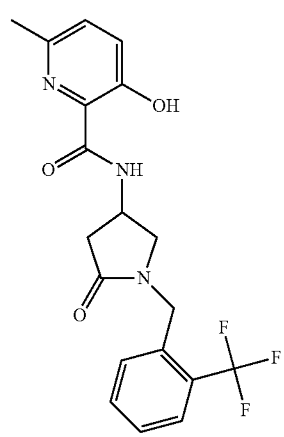 [SMILES: Cc1ccc(O)c(C(=O)NC2CC(=O)N(Cc3ccccc3C(F)(F)F)C2)n1] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202969 | 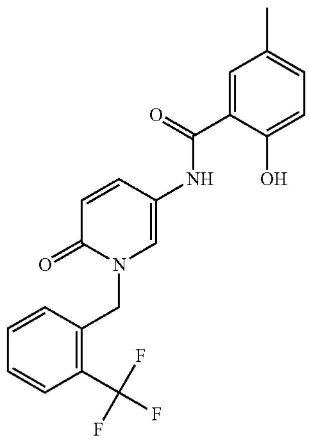 [SMILES: Cc1ccc(O)c(C(=O)Nc2ccc(=O)n(Cc3ccccc3C(F)(F)F)c2)c1] | / |
| NUCC-0202970 | 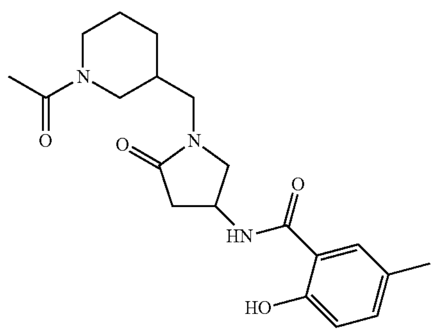 [SMILES: CC(=O)N1CCCC(CN2CC(NC(=O)c3cc(C)ccc3O)CC2=O)C1] | * |
| NUCC-0202971 | 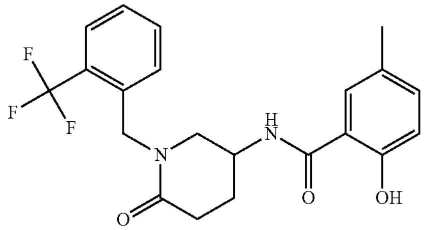 [SMILES: Cc1ccc(O)c(C(=O)NC2CCC(=O)N(Cc3ccccc3C(F)(F)F)C2)c1] | ** |
| NUCC-0202972 | 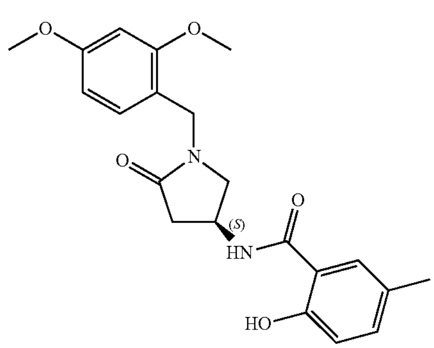 | * |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202973 | 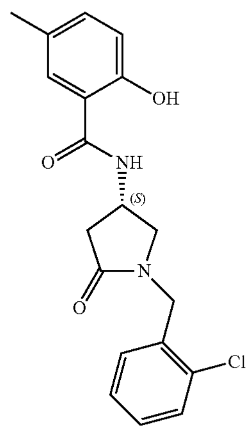 | * |
| NUCC-0202974 | 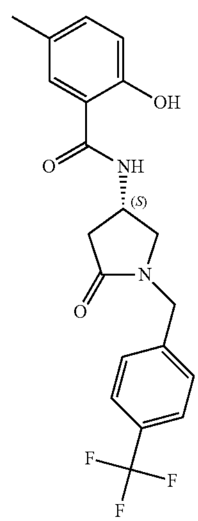 | / |
| NUCC-0202975 | 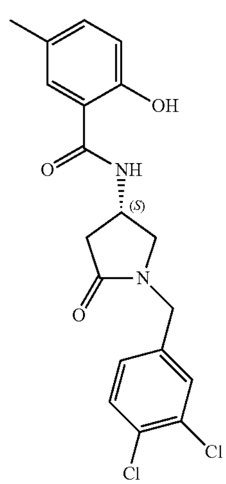 | * |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202976 | 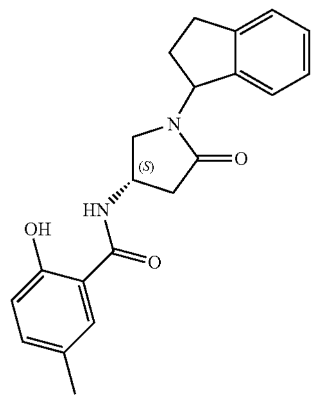 | / |
| NUCC-0202977 | 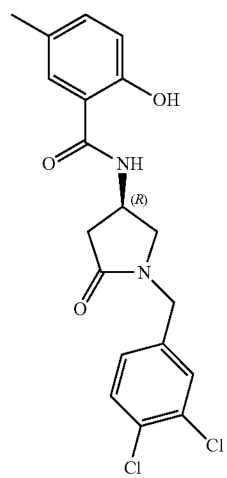 | * |
| NUCC-0202978 | 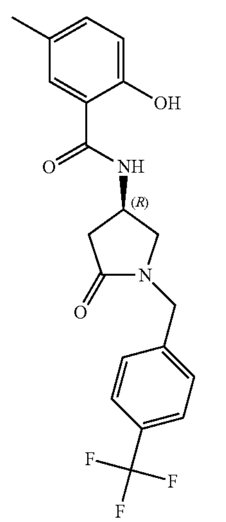 | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0202979 | 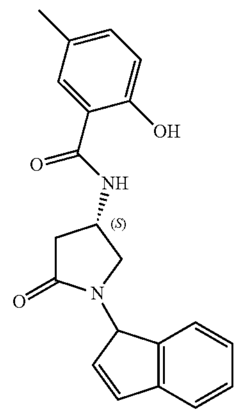 | * |
| NUCC-0223624 | 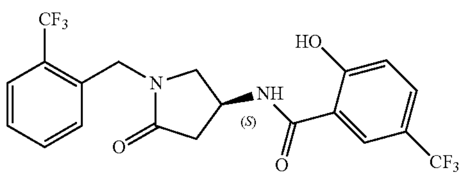 | *** |
| NUCC-0223625 | 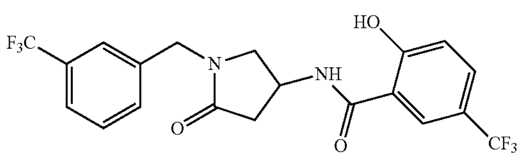 [SMILES: O=C(NC1CC(=O)N(Cc2cccc(C(F)(F)F)c2)C1)c1cc(C(F)(F)F)ccc1O] | *** |
| NUCC-0223626 | 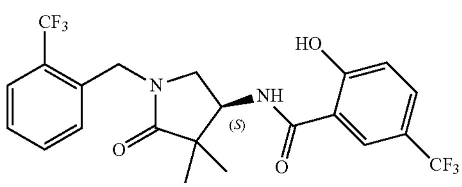 | ** |
| NUCC-0223627 | 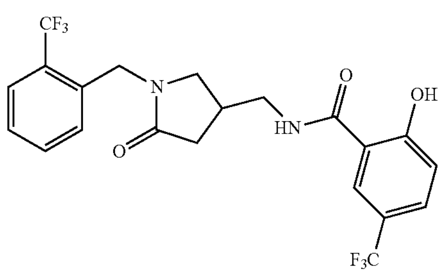 [SMILES: O=C(NCC1CC(=O)N(Cc2ccccc2C(F)(F)F)C1)c1cc(C(F)(F)F)ccc1O] | *** |
| NUCC-0223628 | 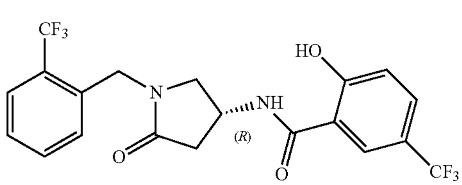 | *** |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0223629 | 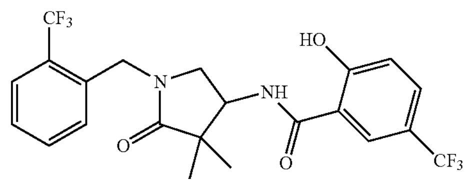 [SMILES: CC1(C)C(=O)N(Cc2ccccc2C(F)(F)F)CC1NC(=O)c1cc(C(F)(F)F)ccc1O] | * |
| NUCC-0223632 | 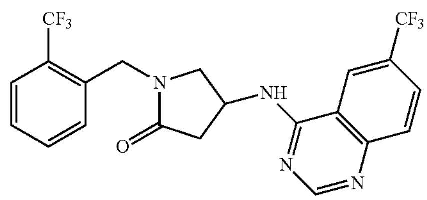 [SMILES: O=C1CC(Nc2ncnc3ccc(C(F)(F)F)cc23)CN1Cc1ccccc1C(F)(F)F] | / |
| NUCC-0223633 | 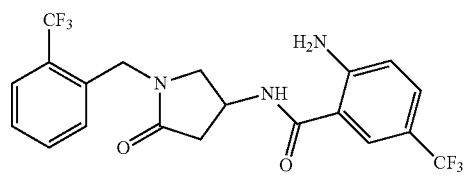 [SMILES: Nc1ccc(C(F)(F)F)cc1C(=O)NC1CC(=O)N(Cc2ccccc2C(F)(F)F)C1] | / |
| NUCC-0223634 | 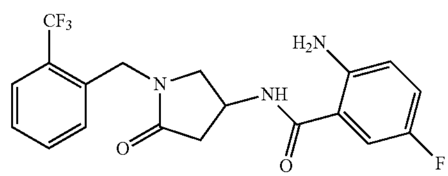 [SMILES: Nc1ccc(F)cc1C(=O)NC1CC(=O)N(Cc2ccccc2C(F)(F)F)C1] | / |
| NUCC-0223635 | 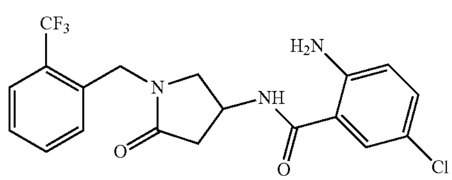 [SMILES: Nc1ccc(Cl)cc1C(=O)NC1CC(=O)N(Cc2ccccc2C(F)(F)F)C1] | / |
| NUCC-0223818 | 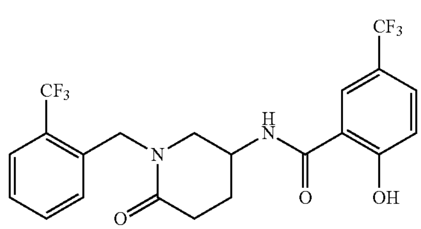 [SMILES: O=C(NC1CCC(=O)N(Cc2ccccc2C(F)(F)F)C1)c1cc(Cl)ccc1O] | ** |
| NUCC-0223819 | 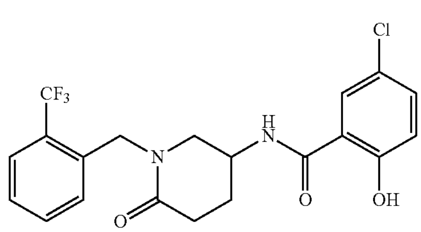 | ** |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0223820 | 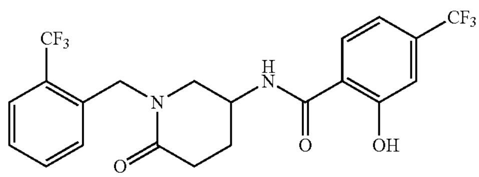 [SMILES: O=C(NC1CCC(=O)N(Cc2ccccc2C(F)(F)F)C1)c1ccc(C(F)(F)F)cc1O] | / |
| NUCC-0223821 | 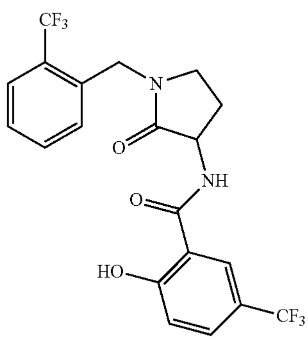 [SMILES: O=C(NC1CCN(Cc2ccccc2C(F)(F)F)C1=O)c1cc(C(F)(F)F)ccc1O] | *** |
| NUCC-0223822 | 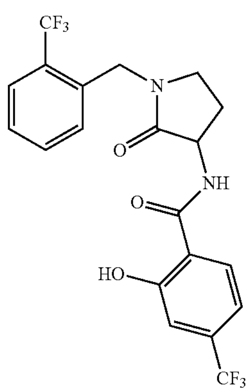 [SMILES: O=C(NC1CCN(Cc2ccccc2C(F)(F)F)C1=O)c1ccc(C(F)(F)F)cc1O] | / |
| NUCC-0223823 | 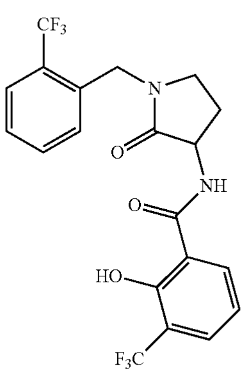 [SMILES: O=C(NC1CCN(Cc2ccccc2C(F)(F)F)C1=O)c1cccc(C(F)(F)F)c1O] | / |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0223824 | 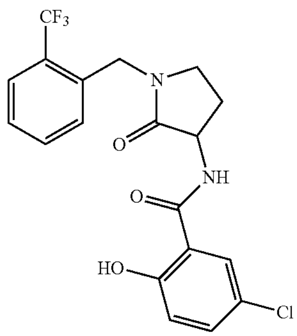 [SMILES: O=C(NC1CCN(Cc2ccccc2C(F)(F)F)C1=O)c1cc(Cl)ccc1O] | / |
| NUCC-0223825 | 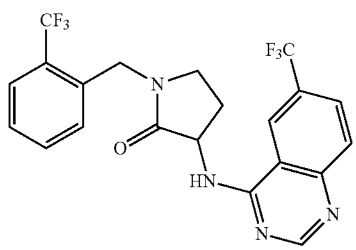 [SMILES: O=C1C(Nc2ncnc3ccc(C(F)(F)F)cc23)CCN1Cc1ccccc1C(F)(F)F] | / |
| NUCC-0223826 | 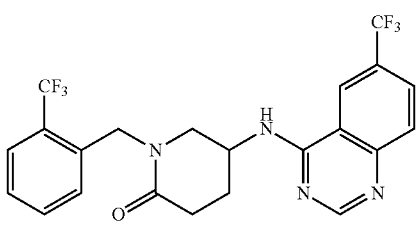 [SMILES: O=C1CCC(Nc2ncnc3ccc(C(F)(F)F)cc23)CN1Cc1ccccc1C(F)(F)F] | / |
| NUCC-0226232 | 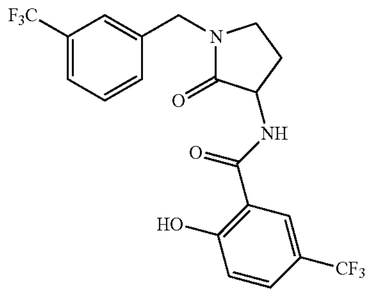 [SMILES: O=C(NC1CCN(Cc2cccc(C(F)(F)F)c2)C1=O)c1cc(C(F)(F)F)ccc1O] | ** |
| NUCC-0226233 | 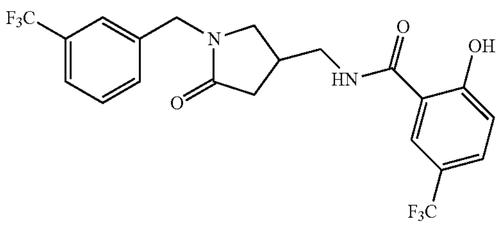 [SMILES: O=C(NCC1CC(=O)N(Cc2cccc(C(F)(F)F)c2)C1)c1cc(C(F)(F)F)ccc1O] | *** |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0226234 | 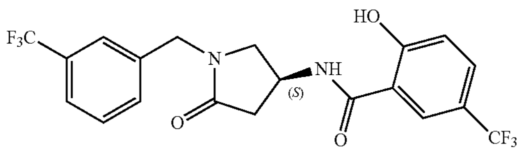 | ** |
| NUCC-0226235 | 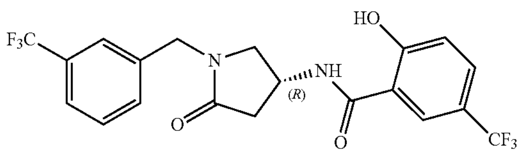 | ** |
| NUCC-0226236 | 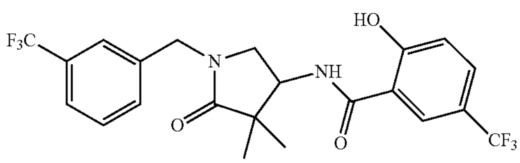 [SMILES: CC1(C)C(=O)N(Cc2cccc(C(F)(F)F)c2)CC1NC(=O)c1cc(C(F)(F)F)ccc1O] | *** |
| NUCC-0226237 | 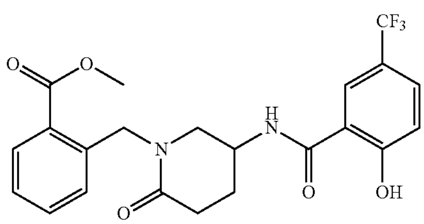 [SMILES: COC(=O)c1ccccc1CN1CC(NC(=O)c2cc(C(F)(F)F)ccc2O)CCC1=O] | ** |
| NUCC-0226238 | 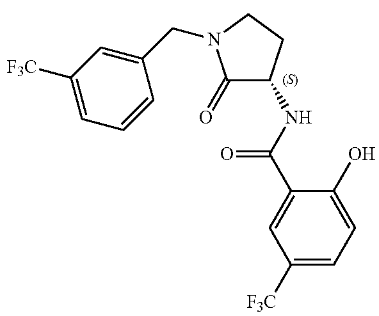 | ** |
| NUCC-0226240 | 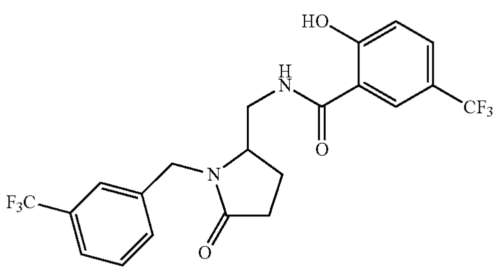 [SMILES: O=C(NCC1CCC(=O)N1Cc1cccc(C(F)(F)F)c1)c1cc(C(F)(F)F)ccc1O] | ** |

TABLE 1-continued

Representative Compounds and Biological Activity

| Molecule Name | Structure | IC50 Potency Code:<br><1 μM: ***<br>1-10 μM: **<br>10-50 μM: *<br>>50 μM: / |
|---|---|---|
| NUCC-0226241 | 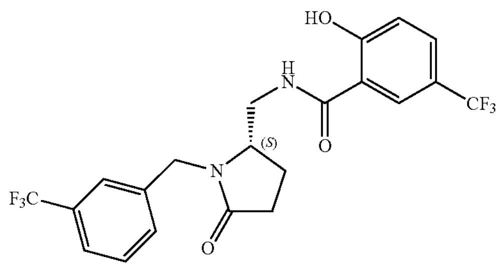 | ** |
| NUCC-0226242 | 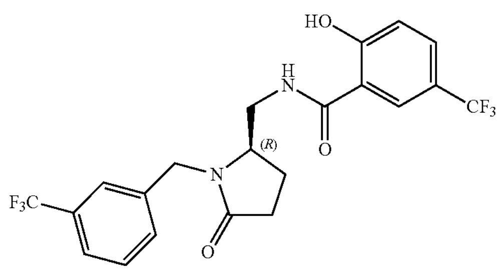 | ** |
| NUCC-0226243 | 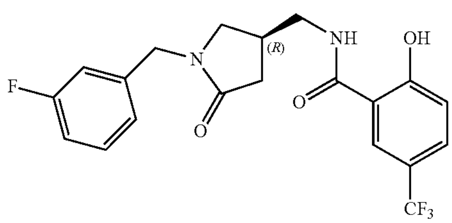 | *** |
| NUCC-0226244 | 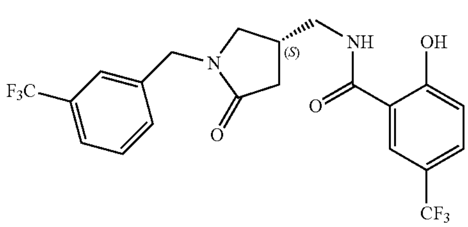 | *** |
| NUCC-0226245 | 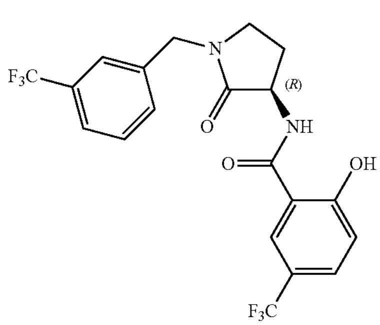 | ** |

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having a formula I:

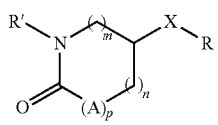

or a pharmaceutically acceptable salt thereof, wherein m is 0-2, n is 0-1, and p is 0-1, with the proviso that (m+n+p) is 2 or 3;
wherein A is —C($R^1$)($R^2$)—;
wherein $R^1$, $R^2$, and $R^3$ are independently selected from hydrogen and alkyl;
wherein R' is selected from hydrogen, alkyl, hydroxyalkyl, cycloalkyl, heterocycloalkyl, alkyl(heterocycloalkyl), aryl, heteroaryl, alkyl(aryl), and alkyl(heteroaryl), and R' is optionally substituted at one or more positions with a substituent selected from alkyl, alkoxy, halogen, haloalkyl, amino, cyano, nitro, aryl, hydroxyl, carboxyl, carboxy(alkyl) ester, acyl, and oxo; and
wherein
X is selected from —N($R^3$)—C(O)—, —N($R^3$)—CH$_2$—, —N($R^3$)—C(O)—CH$_2$—, —N($R^3$)—, —N($R^3$)—S(O)(O)—, and —C(O)—N($R^3$)— and R is selected from hydrogen, alkyl, hydroxyalkyl, cycloalkyl, heterocycloalkyl, alkyl(heterocycloalkyl), aryl, heteroaryl, alkyl(aryl), and alkyl(heteroaryl), and R is optionally substituted at one or more positions with a substituent selected from alkyl, alkoxy, halogen, haloalkyl, amino, cyano, nitro, aryl, hydroxyl, carboxyl, carboxy(alkyl) ester, acyl, and oxo; or
X is —CH$_2$—N($R^3$)—C(O)— and R is selected from hydrogen, alkyl, hydroxyalkyl, cycloalkyl, heterocycloalkyl, alkyl(heterocycloalkyl), aryl, heteroaryl, alkyl(aryl), and alkyl(heteroaryl), and R is optionally substituted at one or more positions with a substituent selected from alkyl, alkoxy, halogen, haloalkyl, unsubstituted amino, cyano, nitro, unsubstituted aryl, hydroxyl, carboxyl, carboxy(alkyl) ester, acyl, and oxo.

2. The compound of claim 1, wherein m=1, n=0, p=1, A is —C($R^1$)($R^2$)—, X is —CH$_2$—N($R^3$)—C(O)—, R is aryl, and R' is alkyl(aryl);
wherein R' is optionally substituted at one or more positions with a substituent selected from alkyl, alkoxy, halogen, haloalkyl, substituted amino, cyano, nitro, substituted aryl, hydroxyl, carboxyl, carboxy(alkyl) ester, acyl, and oxo, and
wherein R is optionally substituted at one or more positions with a substituent selected from alkyl, alkoxy, halogen, haloalkyl, unsubstituted amino, cyano, nitro, unsubstituted aryl, hydroxyl, carboxyl, carboxy(alkyl) ester, acyl, and oxo.

3. The compound of claim 2, wherein $R^1$, $R^2$, and $R^3$ are hydrogen, R is phenyl, and R' is benzyl;
wherein R' is optionally substituted at one or more positions with a substituent selected from alkyl, alkoxy, halogen, haloalkyl, substituted amino, cyano, nitro, substituted aryl, hydroxyl, carboxyl, carboxy(alkyl) ester, acyl, and oxo, and
wherein R is optionally substituted at one or more positions with a substituent selected from alkyl, alkoxy, halogen, haloalkyl, unsubstituted amino, cyano, nitro, unsubstituted aryl, hydroxyl, carboxyl, carboxy(alkyl) ester, acyl, and oxo.

4. The compound of claim 3, wherein R is substituted with at least one hydroxyl and at least one haloalkyl, and R' is substituted with at least one haloalkyl.

5. The compound of claim 4, wherein R is substituted with one hydroxyl and one trifluoromethyl, and R' is substituted with one trifluoromethyl.

6. The compound of claim 1, wherein m=1, n=0, p=1, A is —C($R^1$)($R^2$)—, X is —N($R^3$)—C(O)—, R is aryl, R' is alkyl(aryl).

7. The compound of claim 6, wherein $R^1$ and $R^2$ are alkyl or hydrogen, $R^3$ is hydrogen, R is phenyl, and R' is benzyl.

8. The compound of claim 7, wherein $R^1$ and $R^2$ are methyl.

9. The compound of claim 6, wherein R is substituted with at least one haloalkyl and at least one hydroxyl, and R' is substituted with at least one haloalkyl.

10. The compound of claim 9, wherein R is substituted with one hydroxyl and one trifluoromethyl, and R' is substituted with one trifluoromethyl.

11. The compound of claim 1, wherein m=2, n=0, p=0, X is —N($R^3$)—C(O)—, R is aryl, and R' is alkyl(aryl).

12. The compound of claim 11, wherein $R^3$ is hydrogen, R is phenyl, and R' is benzyl.

13. The compound of claim 12, wherein R is substituted with at least one haloalkyl and at least one hydroxyl, and R' is substituted with at least one haloalkyl.

14. The compound of claim 13, wherein R is substituted with one hydroxyl and one trifluoromethyl, and R' is substituted with one trifluoromethyl.

15. The compound of claim 1 having a formula selected from
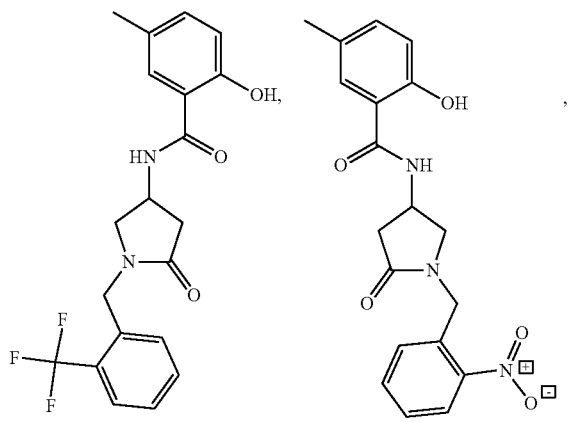
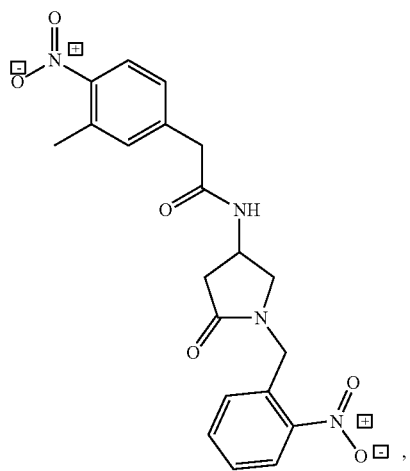
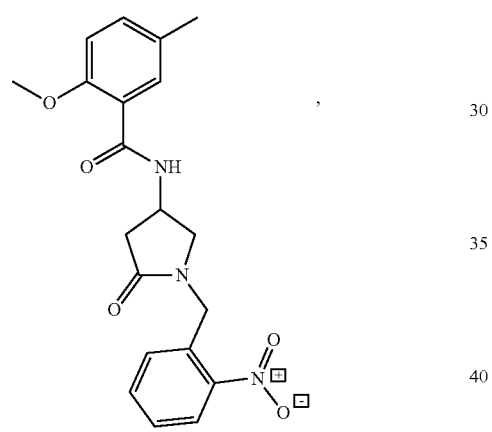
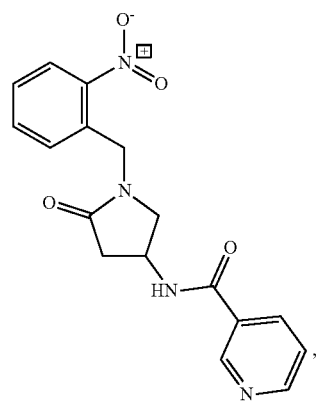
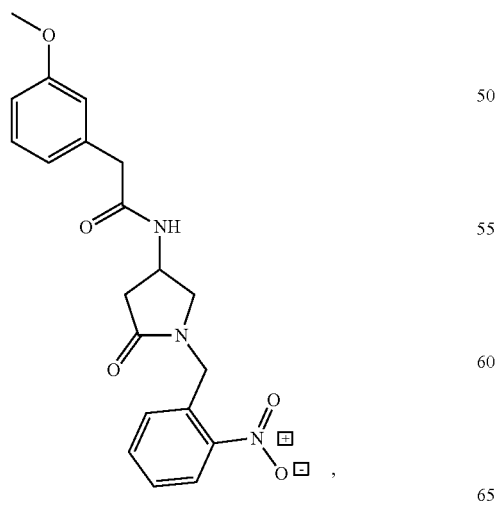
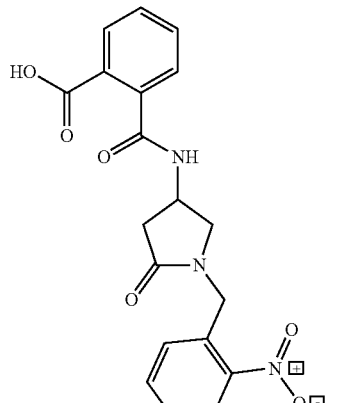

-continued
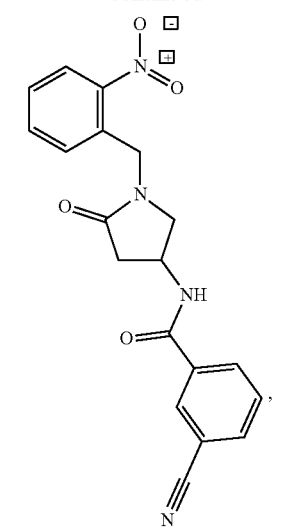
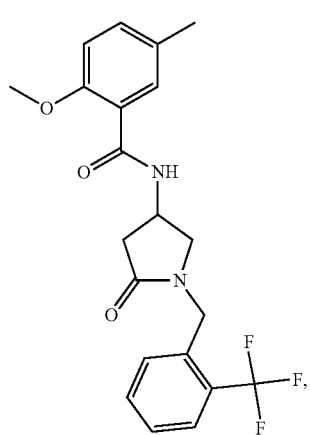
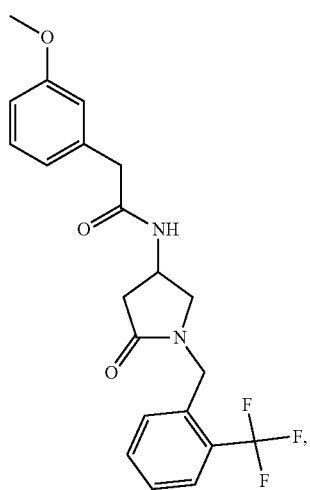
-continued
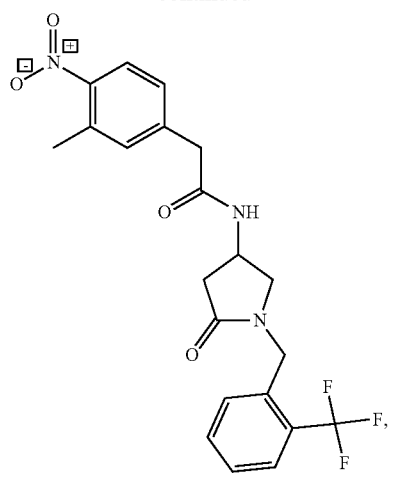
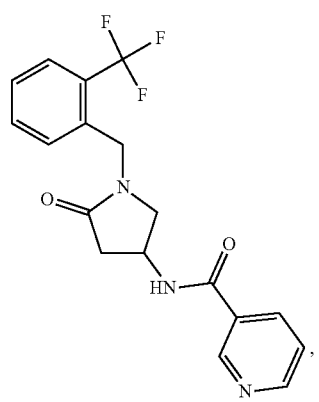
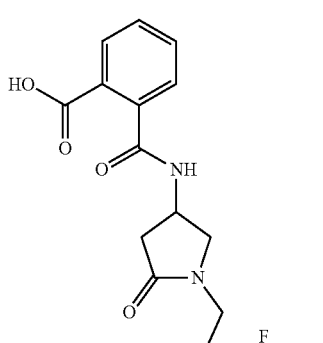
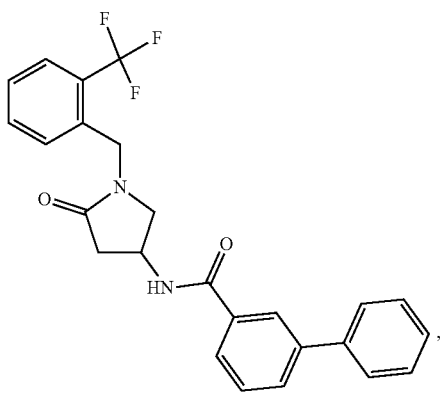

99
-continued
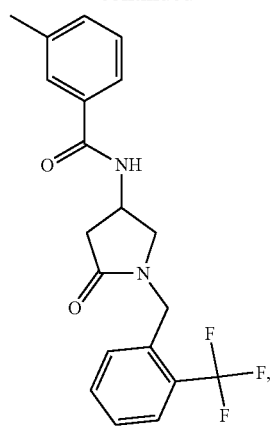
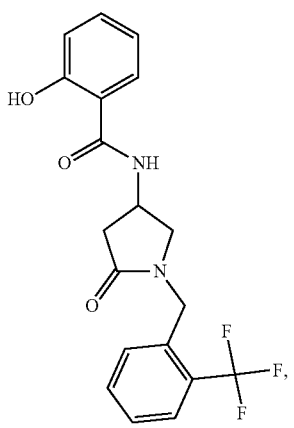
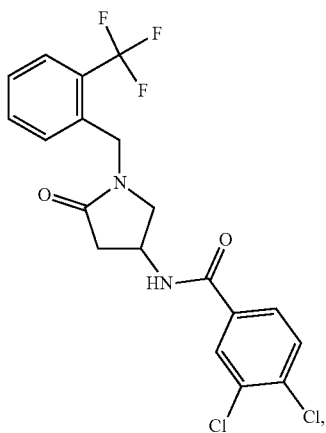
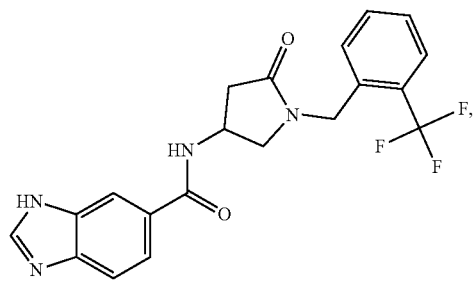
100
-continued
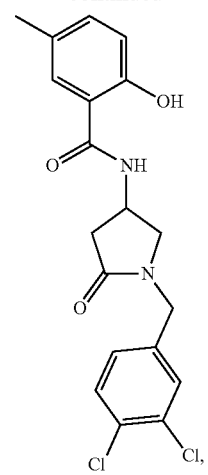
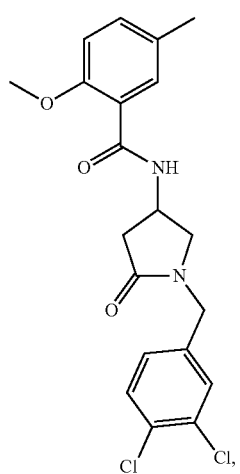
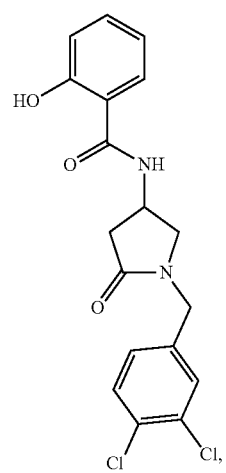

-continued
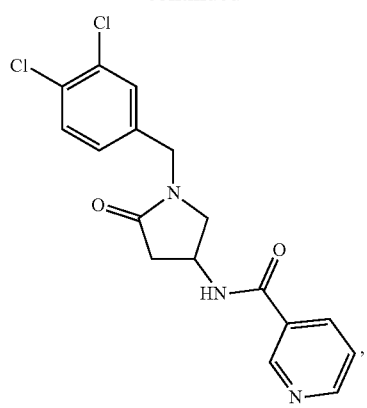
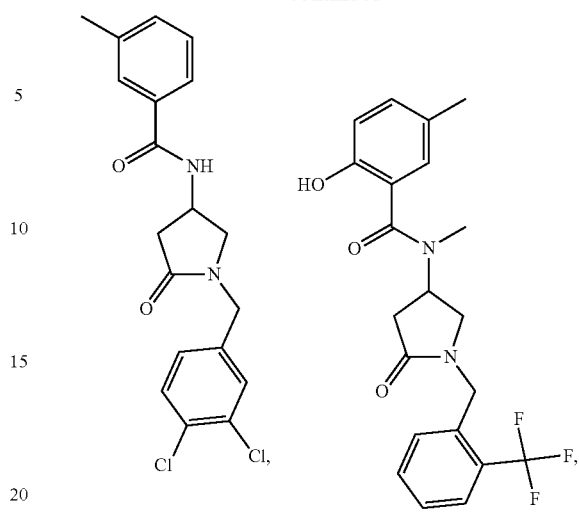
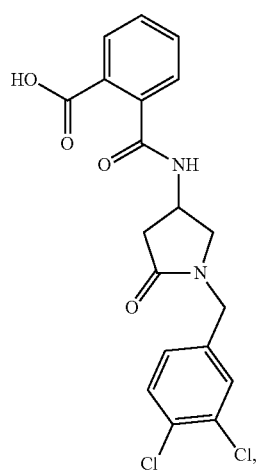
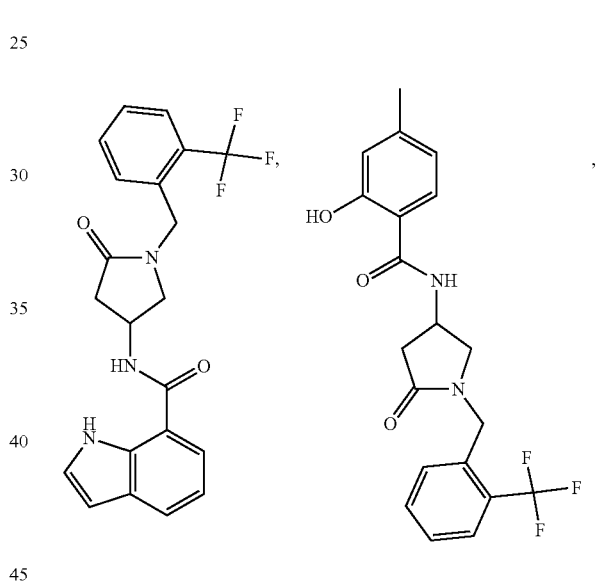
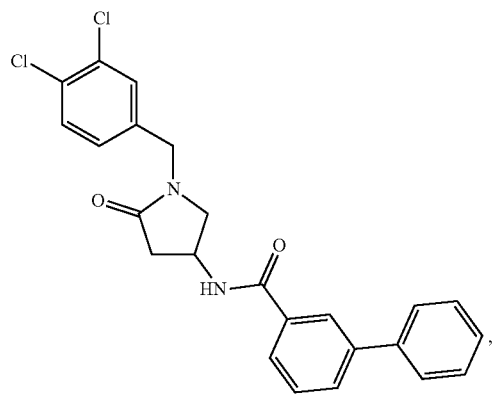
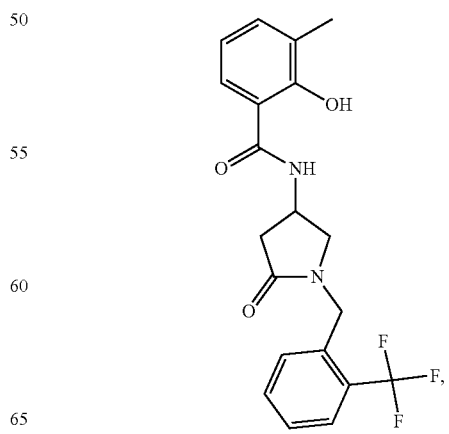

103
-continued
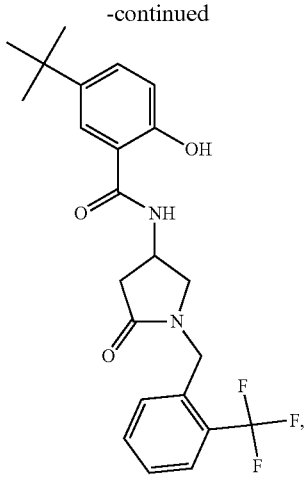
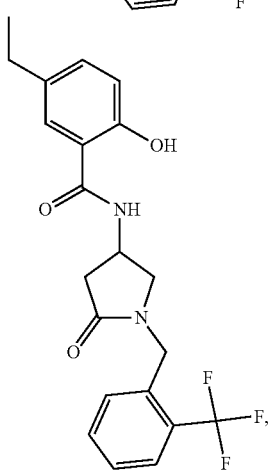
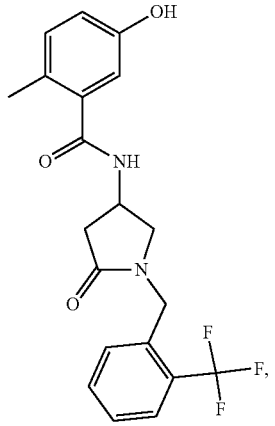
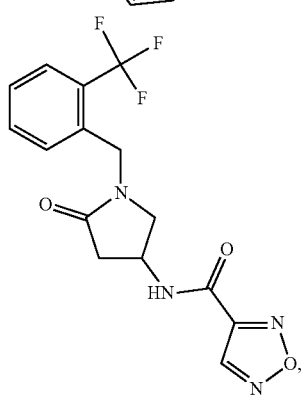
104
-continued
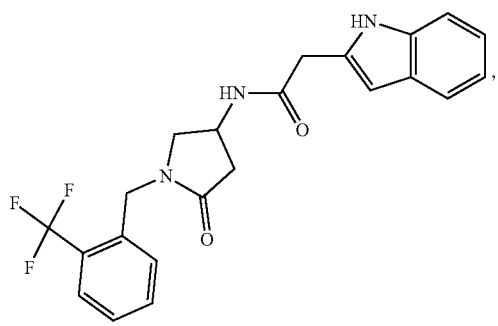
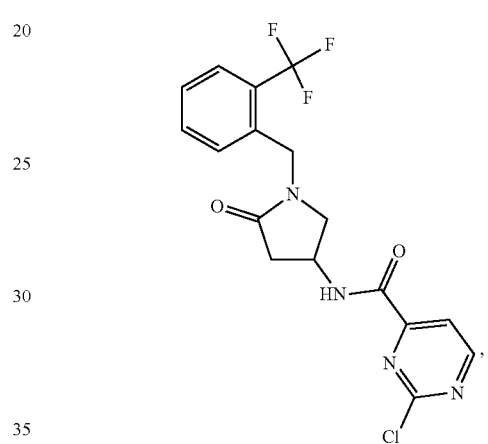
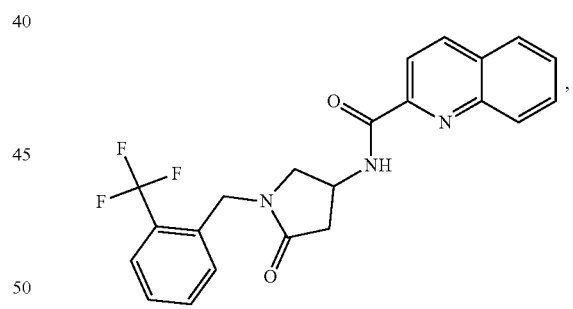

105
-continued
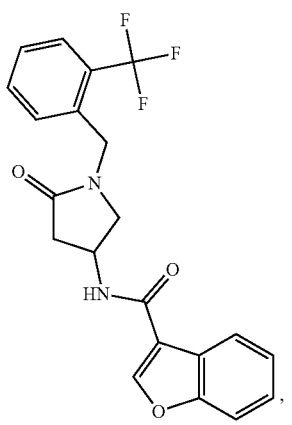
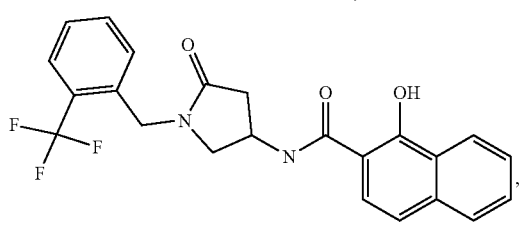
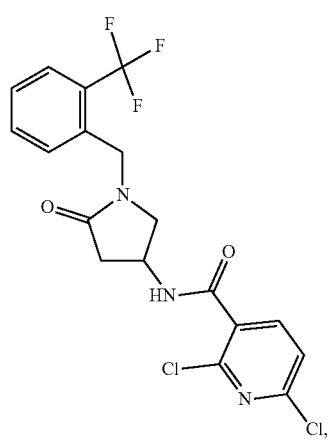
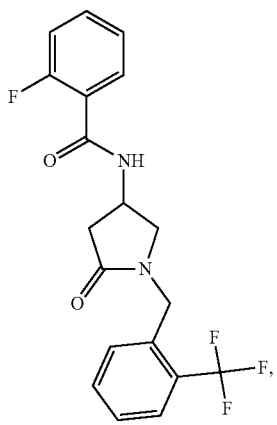
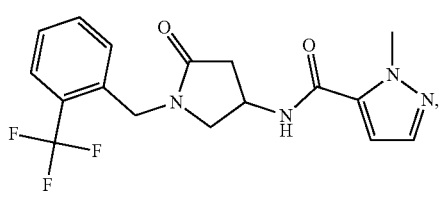
106
-continued
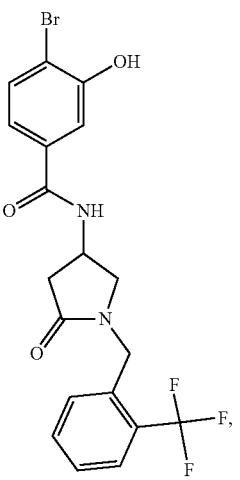
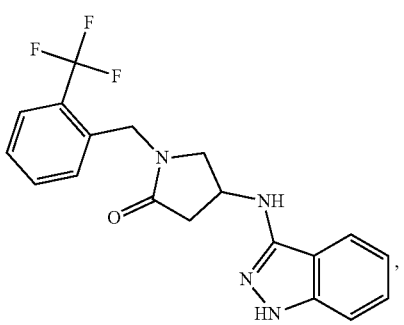
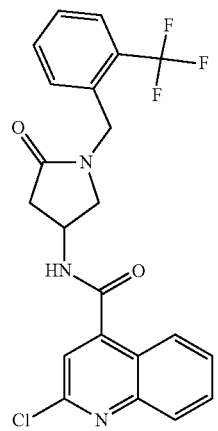
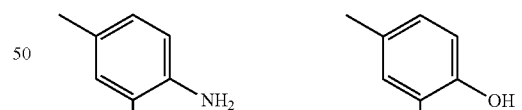
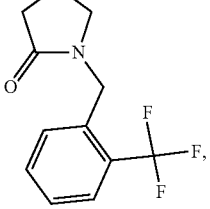
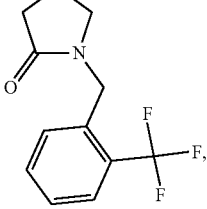

107
-continued
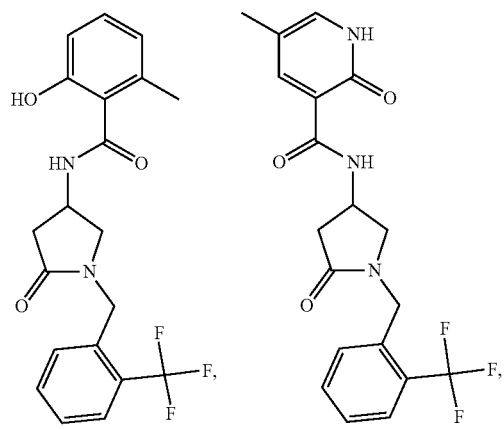
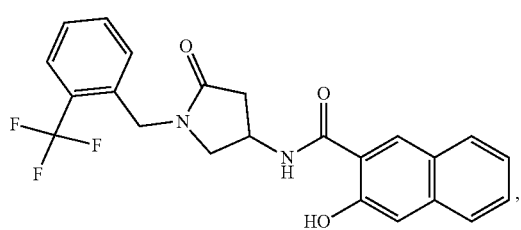
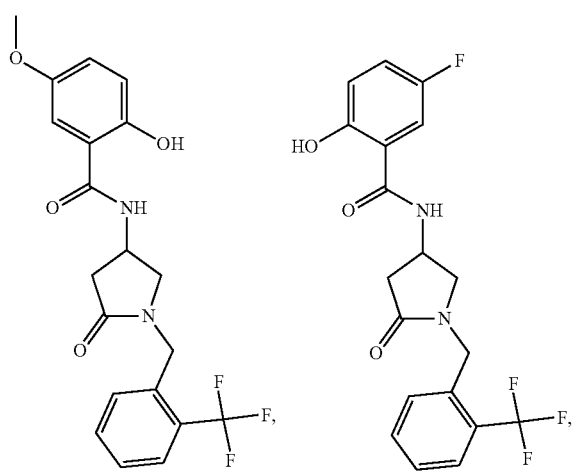
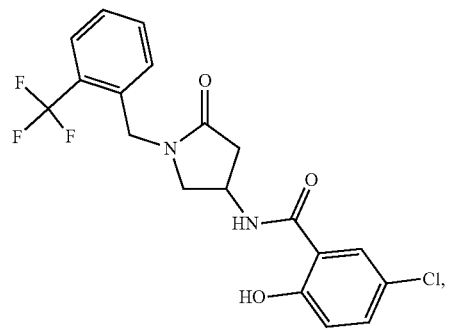
108
-continued
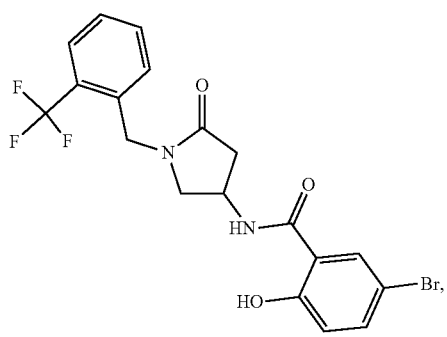
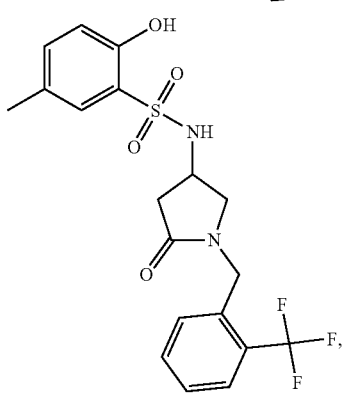
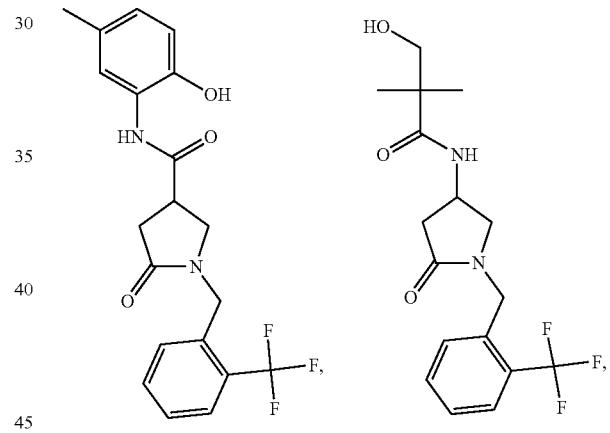
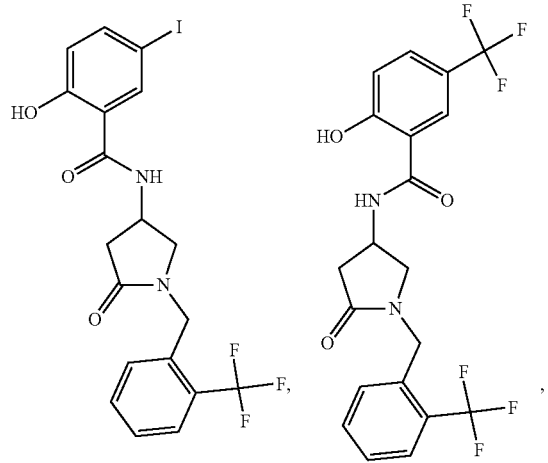

109
-continued
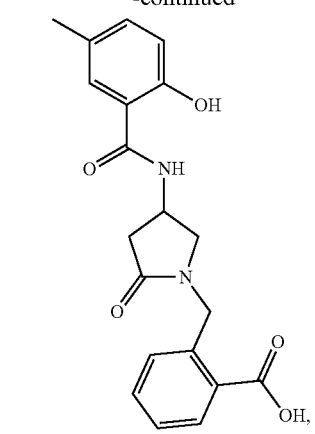
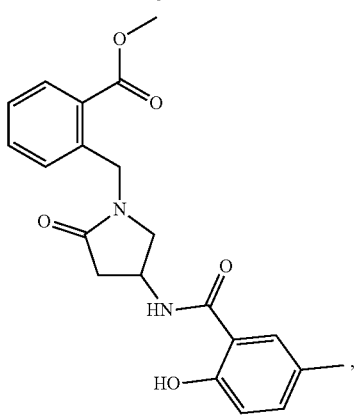
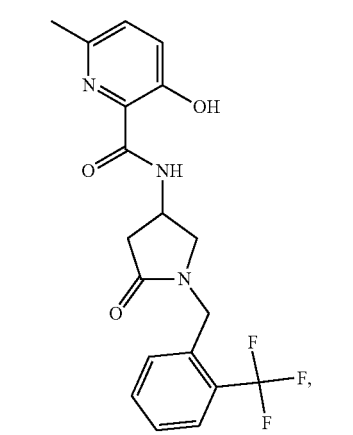
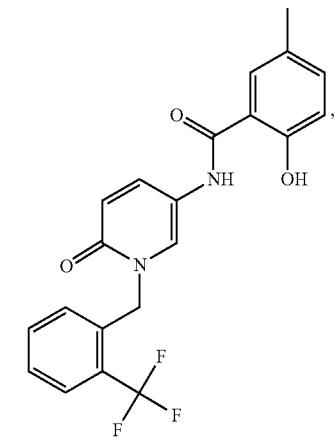
110
-continued
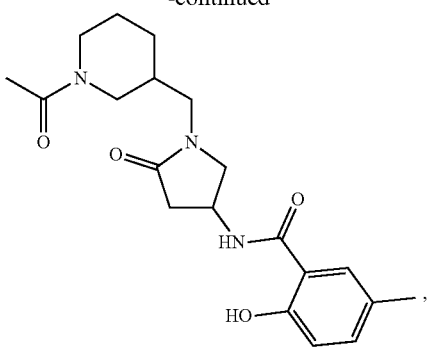
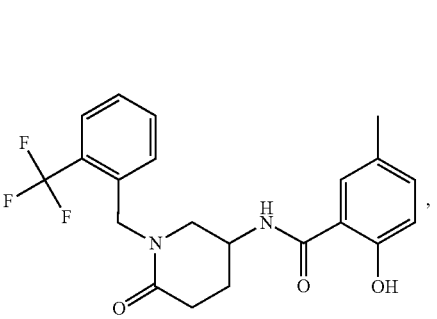
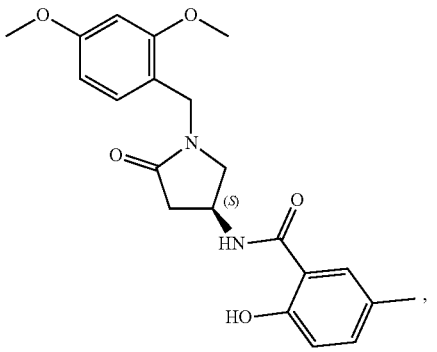
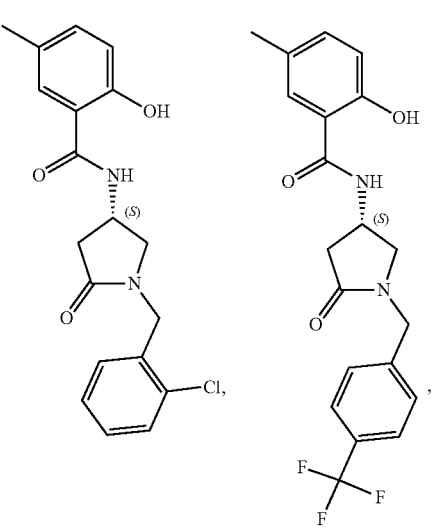

111
-continued
112
-continued
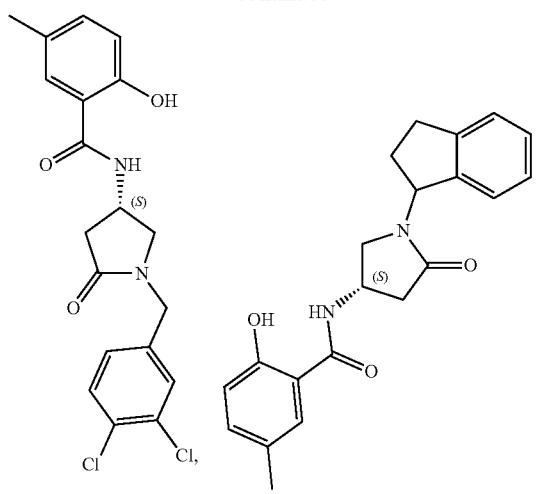
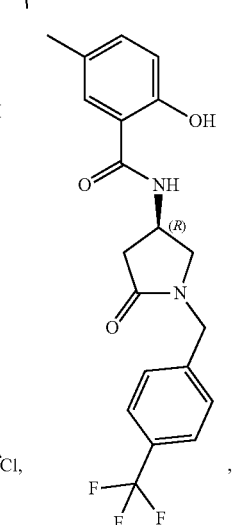
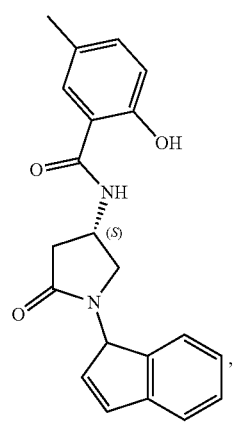
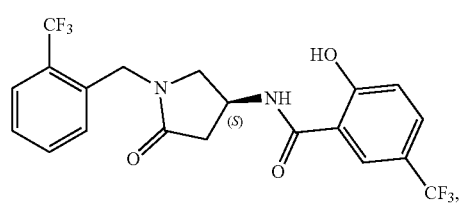
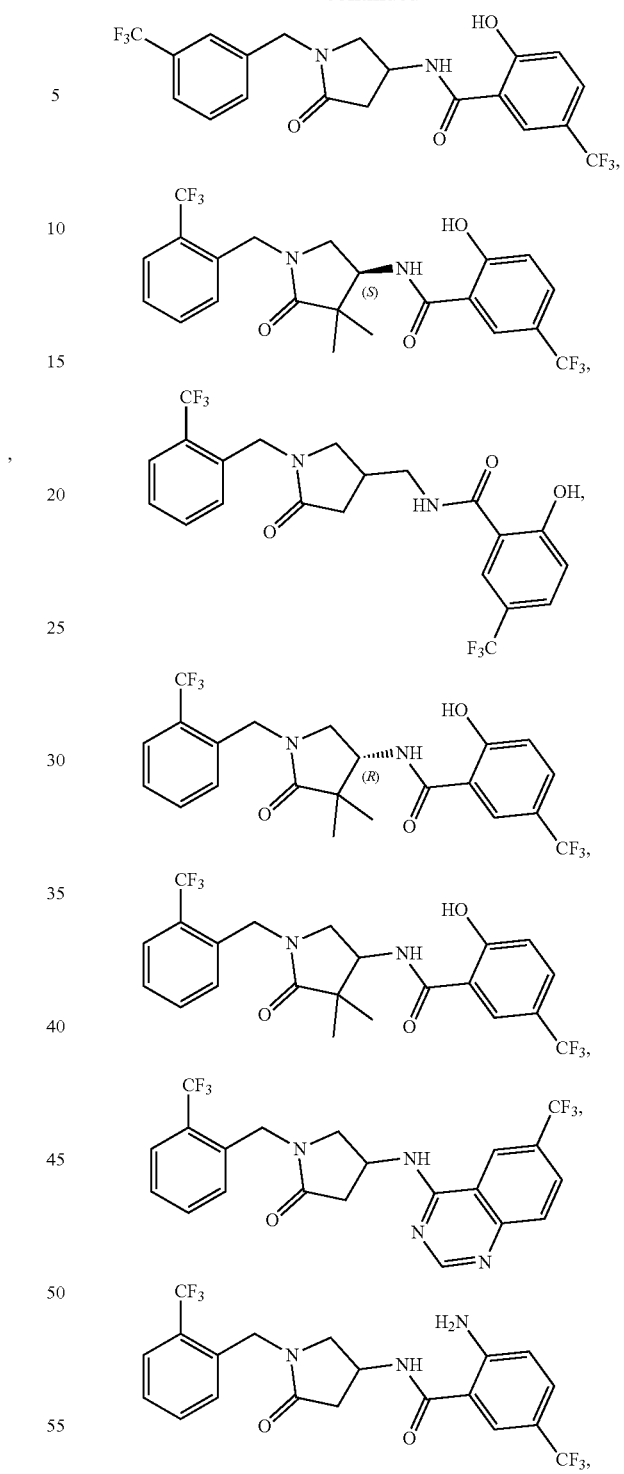
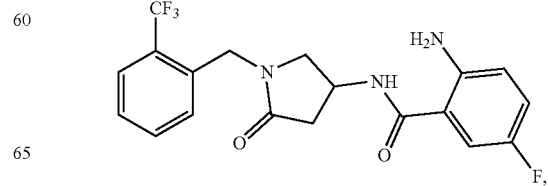

-continued
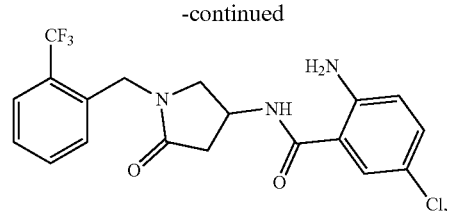
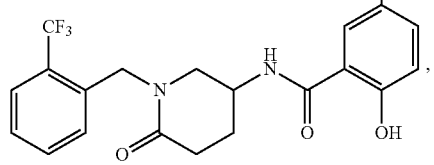
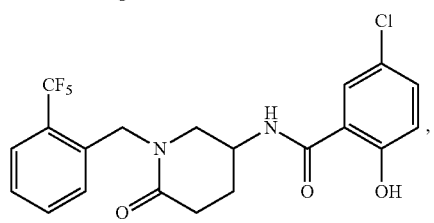
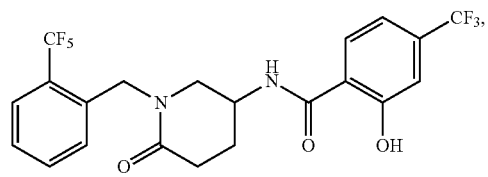
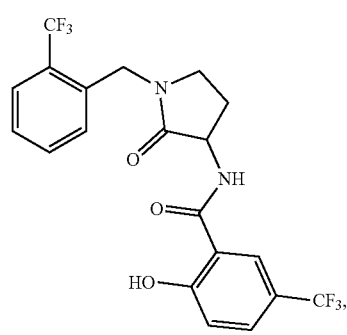
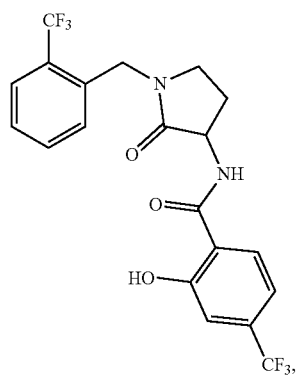
-continued
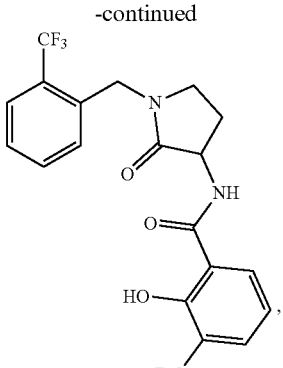
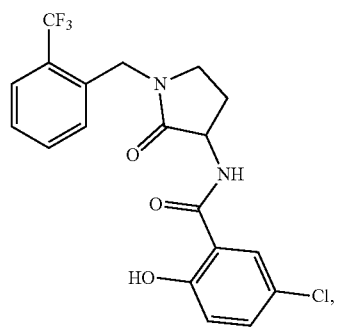
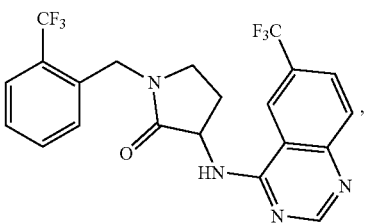
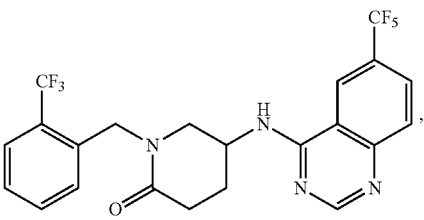
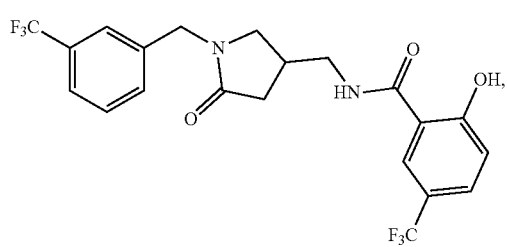

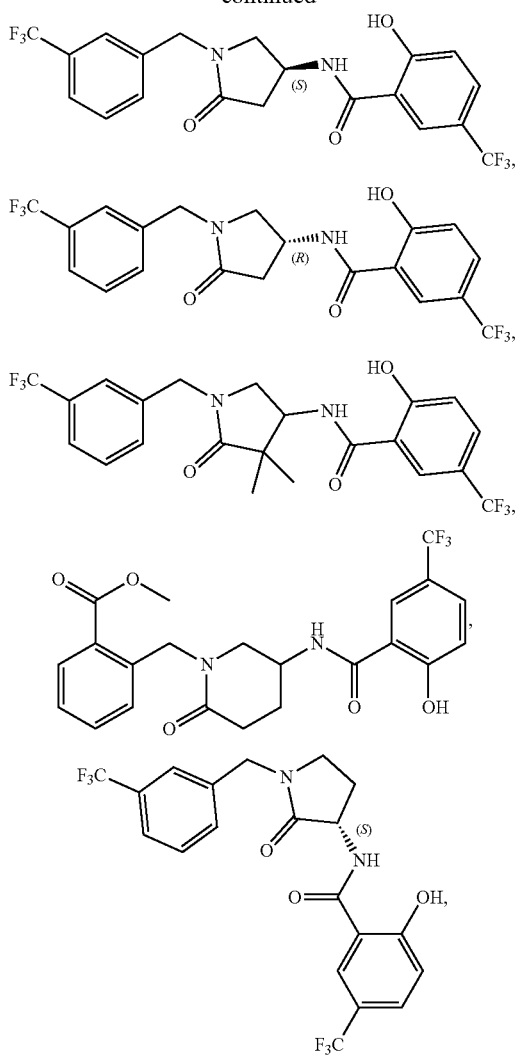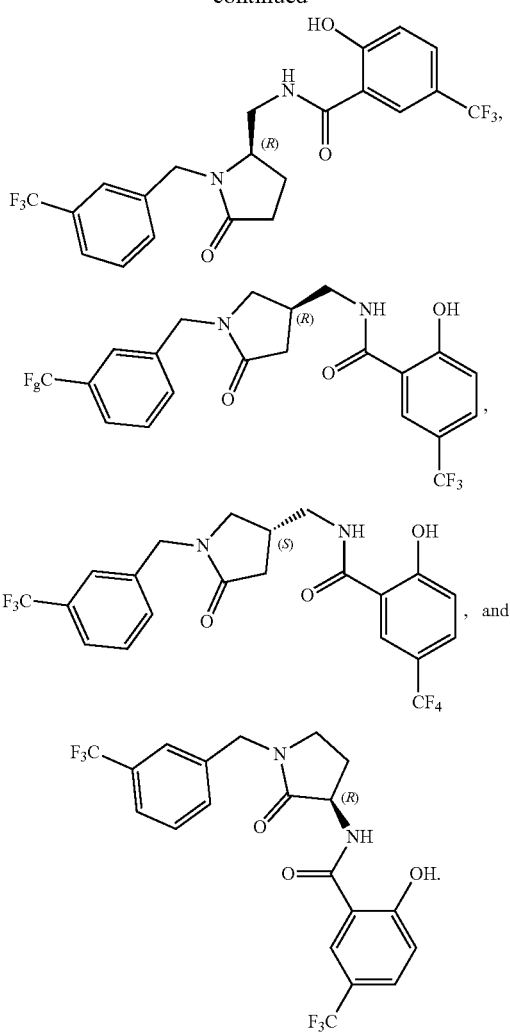
16. The compound of claim 1 having a formula selected from:
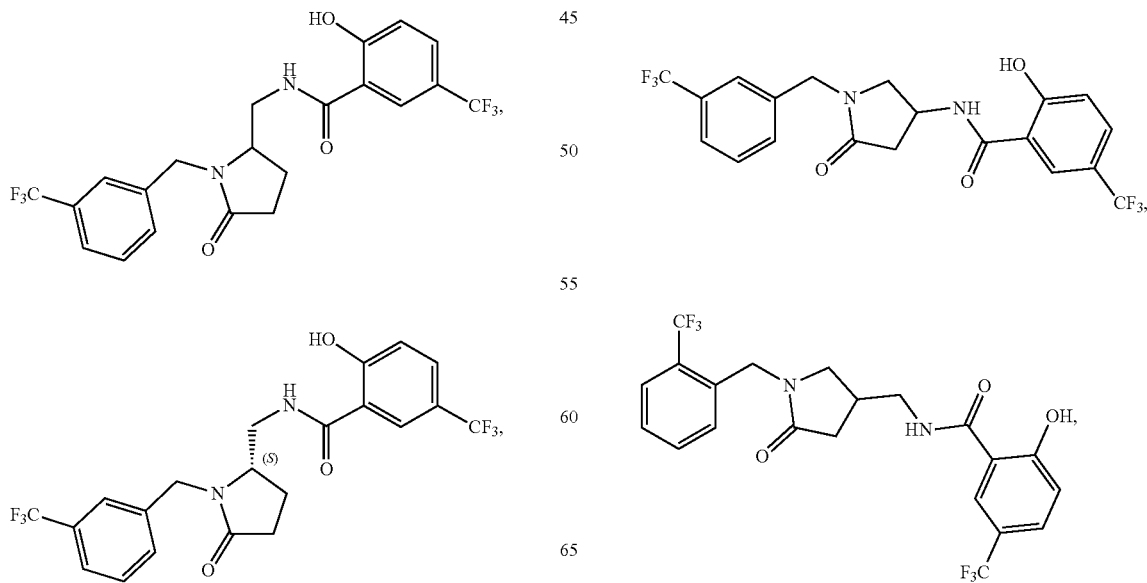

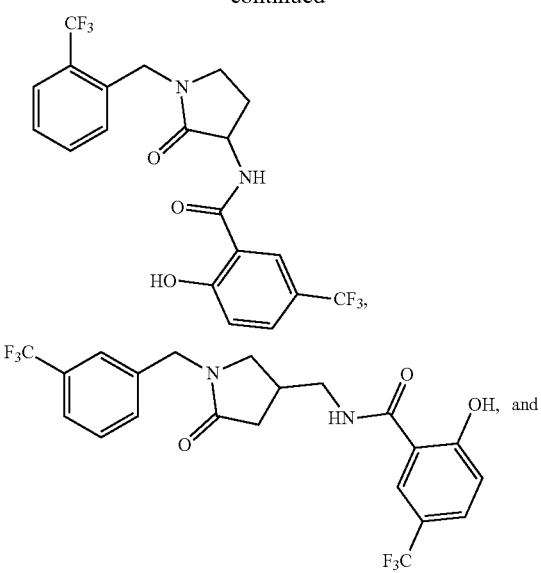

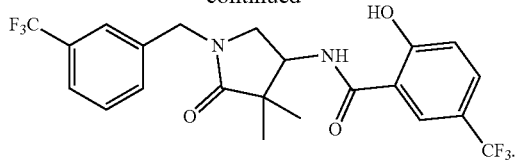

17. A pharmaceutical composition comprising a compound of claim 1 and a suitable pharmaceutical carrier, excipient, or diluent.

18. A method of treating cancer in a subject in need thereof, the method comprising administering the composition of claim 17 to the subject, wherein the cancer is associated with binding of enhancer of zeste homolog 2 (EZH2) and embryonic ectoderm development (EED) protein, and the compound inhibits binding of EZH2 and EED but does not inhibit enzymatic activity of EZH2.

19. The method of claim 18, wherein the cancer is selected from lymphoma, bladder cancer, multiple myeloma, leukemia, non-small cell lung cancer, colon cancer, cancer of the central nervous system, melanoma, ovarian cancer, renal cancer, prostate cancer, and breast cancer.

* * * * *